(12) United States Patent
Placko et al.

(10) Patent No.: US 8,818,075 B2
(45) Date of Patent: Aug. 26, 2014

(54) METHOD FOR ESTIMATING DEFECTS IN AN OBJECT AND DEVICE FOR IMPLEMENTING SAME

(75) Inventors: Dominique Placko, Creteil (FR); Pierre-Yves Joubert, Sceaux (FR); Alain Rivollet, Jouy en Josas (FR)

(73) Assignee: Centre National de la Recherche Scientifique (CNRS) (FR)

( * ) Notice: Subject to any disclaimer, the term of this patent is extended or adjusted under 35 U.S.C. 154(b) by 21 days.

(21) Appl. No.: 13/575,420

(22) PCT Filed: Dec. 28, 2010

(86) PCT No.: PCT/EP2010/070818
§ 371 (c)(1),
(2), (4) Date: Jul. 26, 2012

(87) PCT Pub. No.: WO2011/091932
PCT Pub. Date: Aug. 4, 2011

(65) Prior Publication Data
US 2012/0308120 A1 Dec. 6, 2012

(30) Foreign Application Priority Data
Jan. 26, 2010 (FR) ...................................... 10 50514

(51) Int. Cl.
*G06K 9/00* (2006.01)
*G06K 9/48* (2006.01)
(52) U.S. Cl.
USPC .......................................... 382/149; 382/197
(58) Field of Classification Search
USPC ........................... 382/149, 154, 190, 195, 197
See application file for complete search history.

(56) References Cited

FOREIGN PATENT DOCUMENTS

| FR | 2885697 A1 | 11/2006 |
|---|---|---|
| WO | 2004044790 A1 | 5/2004 |
| WO | 2005001467 A1 | 1/2005 |
| WO | 2007071735 A1 | 6/2007 |
| WO | 2007135265 A1 | 11/2007 |

OTHER PUBLICATIONS

French Preliminary Search Report for Application No. FR1050514 dated Sep. 30, 2010.

(Continued)

*Primary Examiner* — Daniel Mariam
(74) *Attorney, Agent, or Firm* — Lerner, David, Littenberg, Krumholz & Mentlik, LLP

(57) ABSTRACT

The invention relates to a device and method for estimating defects potentially present in an object comprising an outer surface, wherein the method comprises the steps of: a) illuminating the outer surface of the object with an inductive wave field at a predetermined frequency; b) measuring an induced wave field ($\vec{H}$) at the outer surface of the object; c) developing from the properties of the object's material a coupling matrix T associated with a depth Z of the object from the outer surface; d) solving the matrix system $$\left( \begin{bmatrix} \vec{H} \\ \vec{0} \\ \vec{0} \end{bmatrix} = T \cdot \vec{J} \right)$$

to determine a vector ($\vec{J}$) at depth Z; e) extracting a sub-vector ($\vec{J}_S$) from the vector ($\vec{J}$) corresponding to a potential defect on the object at depth Z; and f) quantitatively estimating the potential defect from the sub-vector ($\vec{J}_S$) at depth Z, wherein the method is performed using a computer or processor.

10 Claims, 34 Drawing Sheets

(56) References Cited

OTHER PUBLICATIONS

International Search Report for Application No. PCT/EP2010/070818 dated Mar. 11, 2011.
Le Diraison Y et al: "Characterization of subsurface defects in aeronautical riveted lap-joints using multi-frequency eddy current imaging", NDT & E International, Butterworth-Heinemann, Oxford, GB LNKD-DOI: 10.1016/J.NDTEINT, 2008.10.005, vol. 42, No. 2, (2009), pp. 133-140, XP025916339.
Liebeaux et al., "The DPSM method and its application to NDE problems with intefaces modelling", Eur. Phys. J. Appl. Phys., vol. 38, 2007, pp. 283-286, XP002602974.
Zitouni et al., "Modeling of Intelligent Electromagnetic Sensor for Buried Tags", IEEE Industrial Electronics, IECON 2006—32nd Annual Conference on, IEEE, Piscataway, NJ, USA, Nov. 1, 2006, pp. 2921-2926, XP031076941.

Simulated Defect

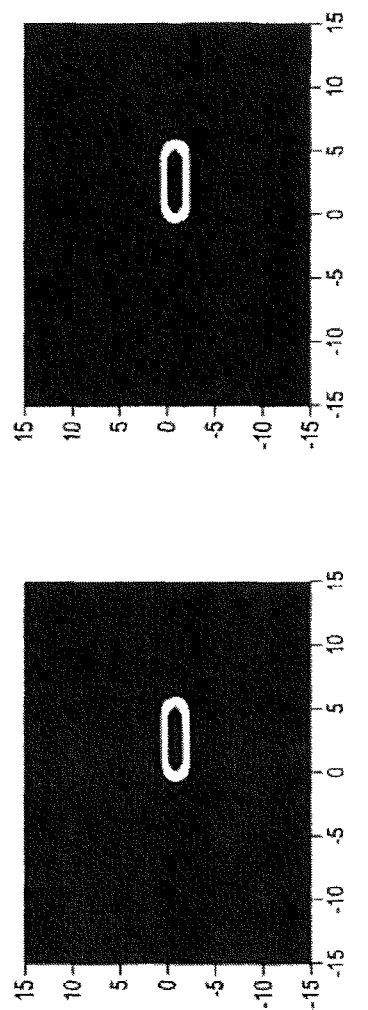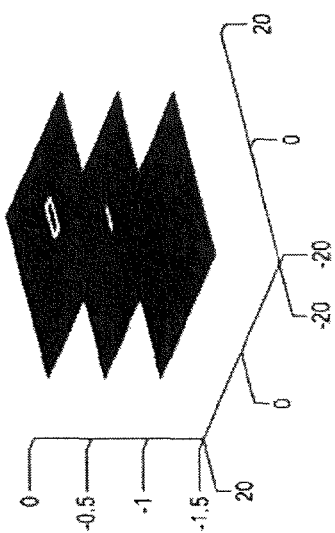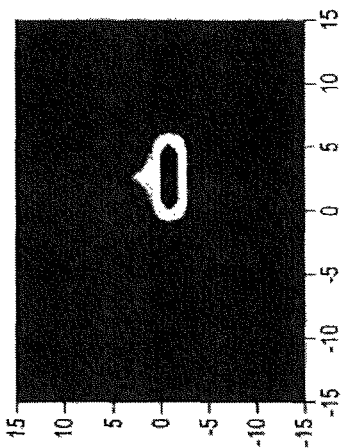
FIG. 20

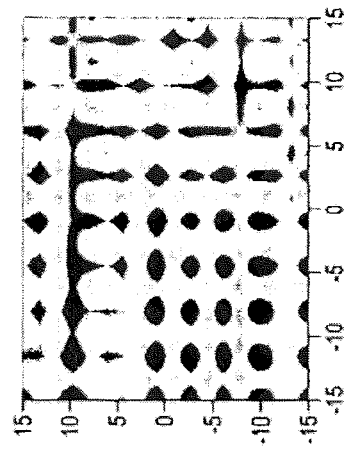
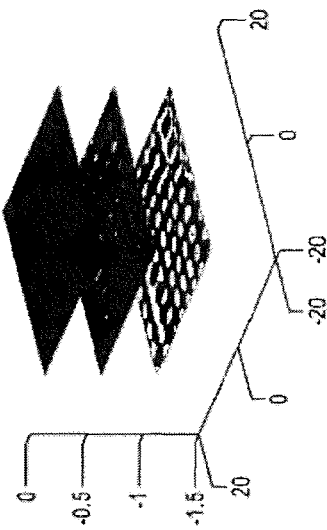
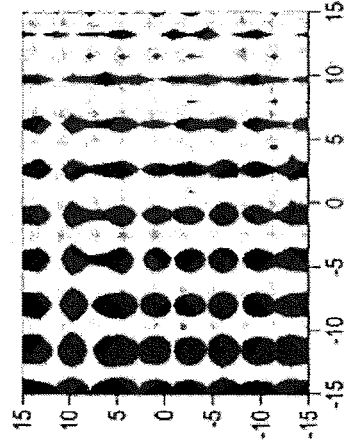
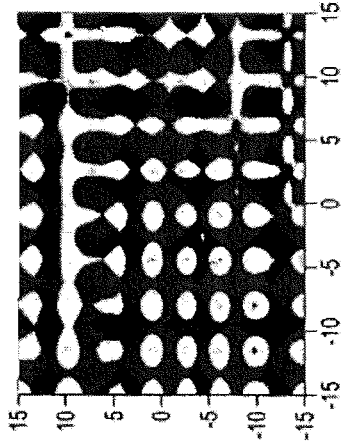
FIG. 21

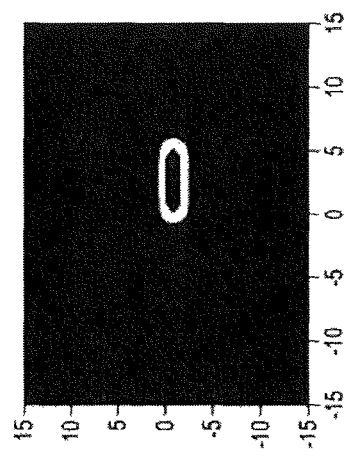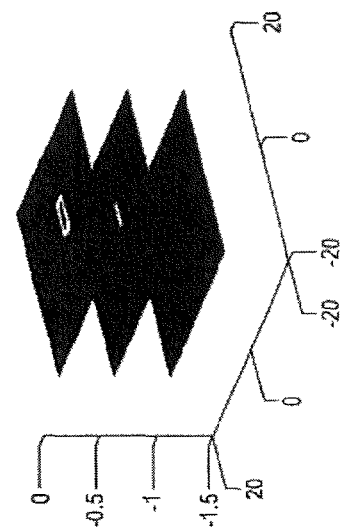
FIG. 23
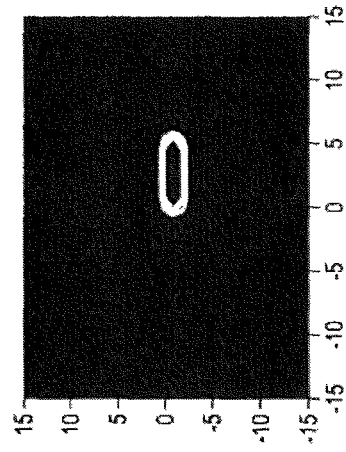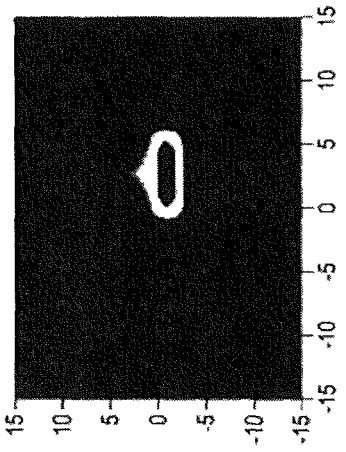

oZ Axis oX Axis oY Axis

FIG. 32
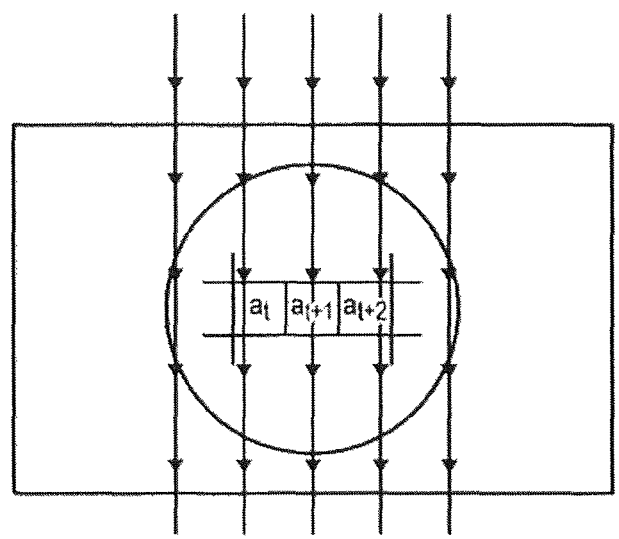
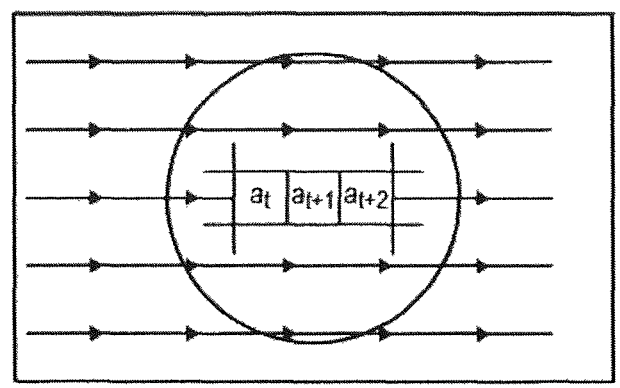

FIG. 33 (a)
Position of defects (circle) and capsule defect
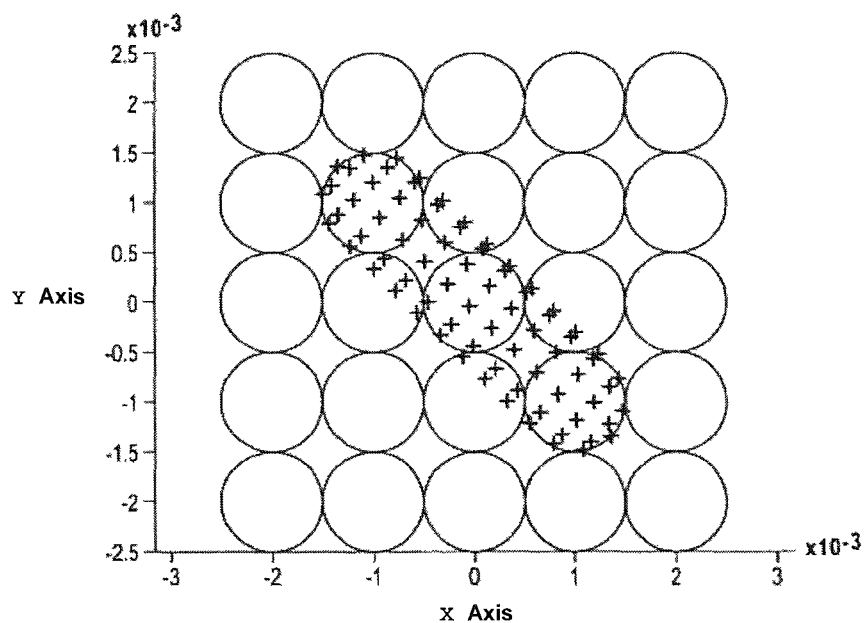
Position of defects (Sphere) and capsule defect
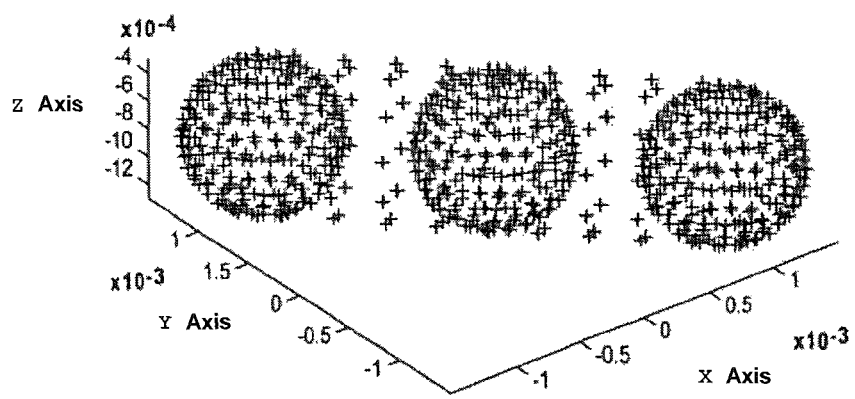

FIG. 33 (b)
Position of defects (circle) and capsule defect
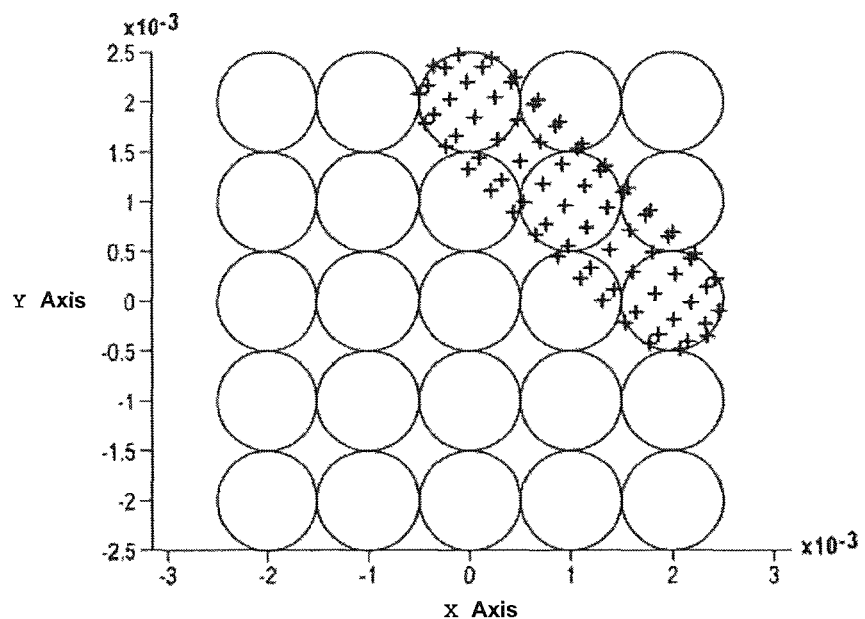
Position of defects (Sphere) and capsule defect
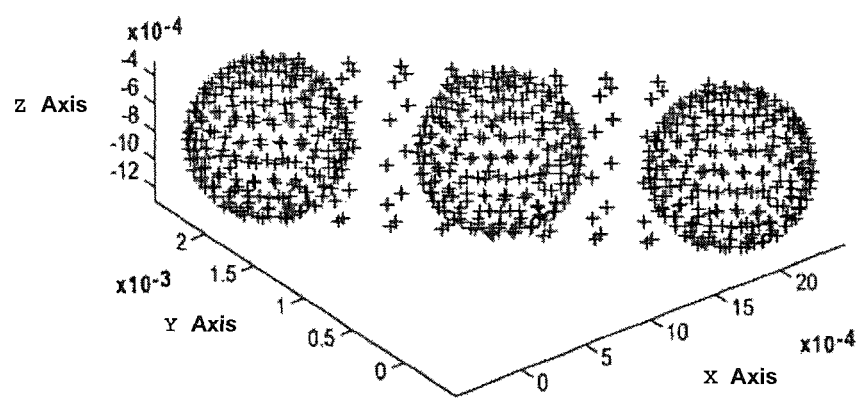

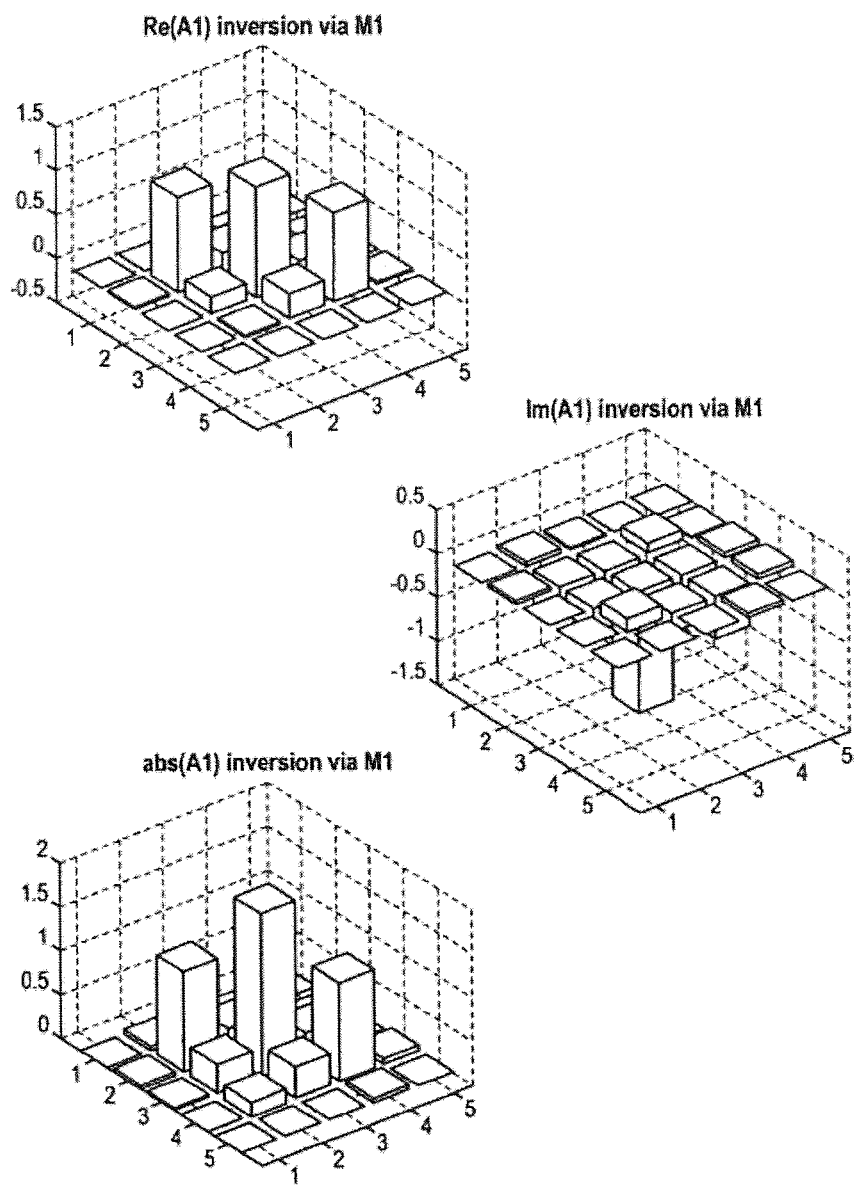

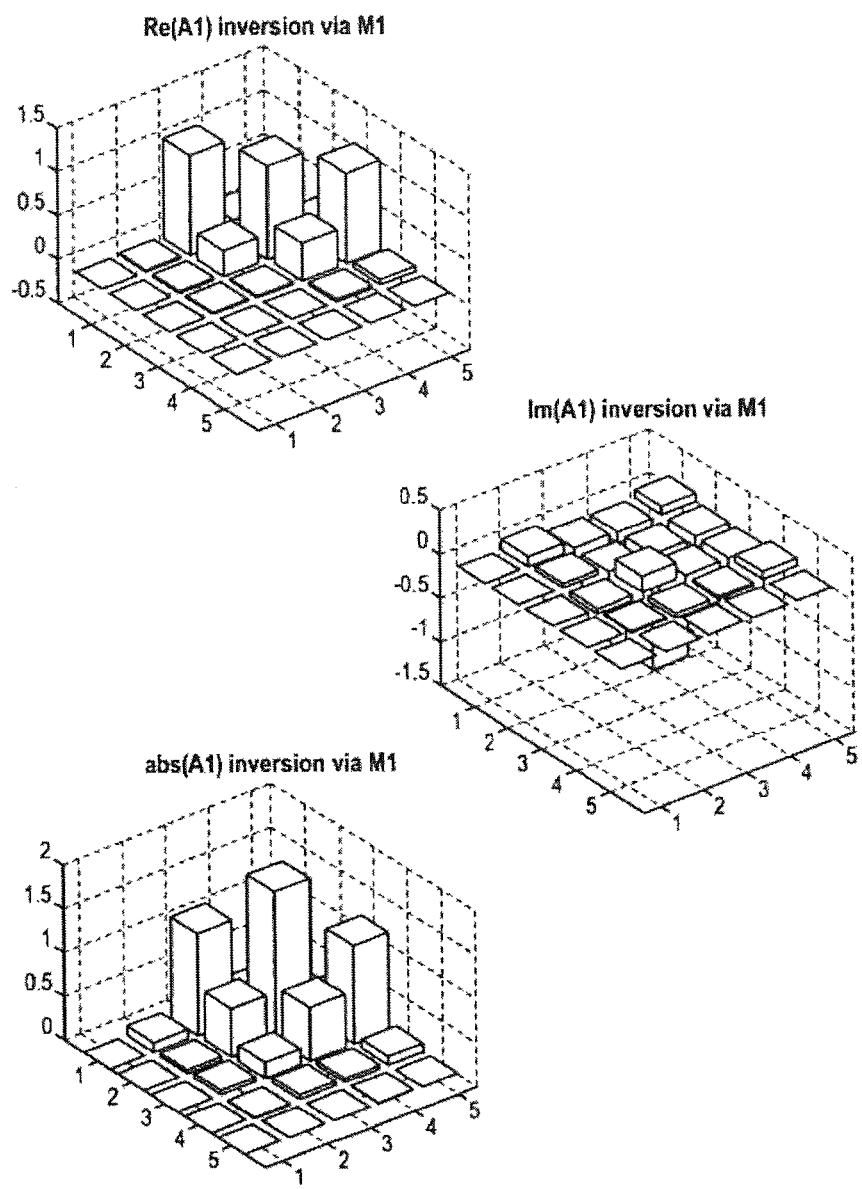

METHOD FOR ESTIMATING DEFECTS IN AN OBJECT AND DEVICE FOR IMPLEMENTING SAME

CROSS-REFERENCE TO RELATED APPLICATIONS

The present application is a national phase entry under 35 U.S.C. §371 of International Application No. PCT/EP2010/070818, filed on Dec. 28, 2010, which claims priority from French Patent Application No. 1050514, filed Jan. 26, 2010, the disclosures of which are incorporated by reference herein.

BACKGROUND OF THE INVENTION

The invention relates to a method for quantitatively estimating defects present in objects or structures, from measurements of physical quantities carried out at the surface, in order to enable a non-destructive evaluation (NDE).

At present, non-destructive control devices generally require the illumination of an object by a wave characterised by one or more physical quantities (magnetic, electric, electromagnetic field, ultrasounds, thermal infrared, X-rays or TeraHz waves, etc.). Said physical quantity, which can be qualified as primary, enters into interaction with the object observed (target), and may be directly behind the phenomenon or the image obtained (absorption of X-rays in the different parts of the human body passed through, for example), or give rise to a secondary quantity. The case of Foucault current imaging may for example be cited, in which the incident electromagnetic wave creates induced current sheets in the material (conductor): it is these current sheets that will be perturbed by a defect, characterised in this case by a variation in the electrical properties of the material (conductivity, permeability, permittivity).

The image of these perturbations is generally obtained by a series of detectors placed on the surface and which give in the best of cases (absence of diffraction, uniform 'illumination' of the object) an image resulting from the superposition of all the properties of the object, throughout its thickness. The simplest example is again that of X-ray radiography in which the image results from all of the parts of the body traversed by the waves, which makes the interpretation difficult. To obtain a 3-dimensional image, it is necessary to 'enrich' all of the signals perceived: this is the X-ray scanner, where N images are obtained for N different observation angles. This case is simpler than most non-destructive control (NDC) problems: absence of diffraction, and access to the two 'faces' of the object to be imaged.

In industrial NDC, there is very rarely access to the two faces of the object or the structure to be controlled, and the use of this type of technique is then very often impossible: it is necessary to resort to the use of Foucault currents, ultrasounds, infrared sensors, etc. These sensors give images very far removed from the real shape of the defects for two major reasons:
  on the one hand, there is a superposition of the images observed (there may be several cracks buried under the inspected surface), and
  on the other hand, the image may result from the perturbation of the secondary quantity.

For example, FIG. 1 shows the image of the real part (Real) and the imaginary part (imag) of a magnetic field on the surface of a conductive material (2017A, formerly Au4G) comprising an emerging crack. This image has been obtained with a Foucault current imager with magneto-optic detection (ECI) as described in the documents WO2005/001467 and WO 2007/135265, to which it is possible to refer for further information. The axes X and Y are in tenths of millimeters.

In this example, with reference to FIG. 2, it is possible to consider that the illumination of the magnetic field has induced current sheets (1) oriented along the axis Y (in the inspected zone), in which the presence of said emerging crack (2) has modified the path, creating by induction a field (3,4) detectable at the surface. There are several problems for 'reconstructing' the real geometry of the defect: the current sheets are different in each plane of depth Z, the defect can thus affect several, and the measuring device does not always give all of the components of the physical quantity radiated by the defect to the surface (magnetic or electric field, in the case of the ECI).

BRIEF SUMMARY OF THE INVENTION

An aim of the invention is to provide a method for estimating defects present in objects (or structures) not having the aforementioned defects and drawbacks.

To this end, according to the invention, a method is provided for quantitatively estimating defects potentially present in an object comprising at least one outer surface, wherein the method comprises the steps of:
  a) "illuminating" the outer surface of the object with an inductive wave field at a predetermined frequency;
  b) measuring, at the outer surface of the object, an induced wave field ($\vec{H}$);
  c) developing, from the properties of the object's material, a coupling matrix T associated with a depth Z of the object from the outer surface;
  d) solving the matrix system $$\left( : \begin{bmatrix} \tilde{H} \\ \tilde{O} \\ \tilde{O} \end{bmatrix} = T\tilde{J} \right)$$

in order to determine a vector $\vec{J}$ at depth Z;
  e) extracting a sub-vector $\vec{J}_S$ of the vector $\vec{J}$, corresponding to a potential defect in the object at depth Z; and
  f) quantitatively estimating the potential defect from the sub-vector $\vec{J}_S$ depth Z.

Advantageously, but optionally, the method according to the invention has at least one of the following characteristics:
  during step f), a sub-step f1) of screening is carried out in order to only keep the components of the sub-vector $\vec{J}_S$ which a phase and a module of induced wave field at depth Z, which these components represent, are in harmony with those of the inductive wave field;
  for a depth Z, the steps a) to f) are carried out for at least two "illuminating" orientations of the outer surface of the object with an inductive wave field;
  the at least two estimations obtained according to the at least two "illuminations" are merged by means of a principal components analysis to obtain a quantitative estimation of the potential defect at depth Z;
  the method moreover comprises a step of three dimensional reconstruction of the potential defect by repeating n times the steps a) to f) for n separate depths Z;
  during the step of three-dimensional reconstruction, a prior sub-step of progressive screening is carried out to perform the n quantitative estimations;

for an iteration p, 1<p<=n, from the field measurement $\vec{H}(Z_p)$ subtracted all or part $\vec{H}_L'(Z_{p-1})$ of the screened field measurement $\vec{H}(Z_{p-1})$, according to the formula $\vec{H}(Z_p) = \vec{H}^{relevé}(Z_p) - K \cdot \vec{H}'(Z_{p-1})$ where K is a reinjection coefficient comprised between 0 and 1 and $\vec{H}$ measurement $(Z_p)$ is the measurement of step b);

the components of $\vec{H}_Z'(Z_{p-1})$ correspond to the potential defect estimated during the iteration p−1, or to the edges of said defect; and, for a given depth Z, a specific predetermined frequency is associated for the inductive wave field used in step a).

According to the invention, a device is moreover provided for quantitatively estimating defects potentially present in an object comprising means for emitting an inductive wave field, means for recording a measurement of an induced wave field on a surface of the object, and processing means intended to implement a method having at least one of the preceding characteristics.

BRIEF DESCRIPTION OF THE DRAWINGS

Other advantages and characteristics of the invention will become clearer from the following description of an embodiment applied to Foucault currents; in the appended drawings:

FIGS. 16 to 23 illustrate the application of the method according to the invention using separate frequencies as a function of the estimation depth;

FIG. 32 illustrates another example of Foucault current application of the tomography of FIG. 30; and, FIGS. 33 to 35 illustrate an application of tomography to a capsule shaped defect at 45° in a block of material made of aluminium.

DETAILED DESCRIPTION

I—Principle of the Method

The principle of the method according to the invention consists in developing global equations of an interaction between a wave and an object to obtain a model of an image perceived by an instrumentation system (here by way of non limiting example a Foucault current imager with magneto-optic detection (ECI) as described in the documents WO2005/001467 and WO 2007/135265). A step of inversion of these global equations makes it possible to 'go back to' the perturbation affecting a secondary quantity (in the ECI system that serves here as example, the excitation current sheets), then to the characteristics of the defect itself, namely in this case the variations in conductivity.

It is obviously understood that this example serves as central thread, but the method according to the invention remains applicable to any system in which the propagation equations of quantities are known, in particular to any system implementing wave phenomena. Furthermore, it should be noted that the term "object" designates a single object, or a set of objects, or instead one or more structures, intended to be analysed for estimation of defects according to the method according to the invention The first problem is that it is virtually impossible, except in simple 'canonic' cases, to develop said equations in an analytical manner. The proposed solution, on which the method according to the invention is based, consists in introducing into the problem governing the interaction of the different environments of the object considered the notion of coupling matrix. This concept stems directly from the application of the method known as 'DPSM' (Distributed Points Sources Method), which is described in greater detail in the documents WO2004/044790 and WO2007/071735, to which it is possible to refer for more information.

The idea of the DPSM method consists in meshing the objects or the interfaces of the object and associating with each of the elementary meshes a test point situated at the barycentre of the mesh, and points sources situated on either side of the test point. Consequently, the initial problem, complex and continuous, gives way to a set of analytical equations making it possible to obtain the physical quantities in all the environments, by simple superposition of the contributions of each radiating source in the considered environment. The actual value of the sources is obtained by resolution of a set of N equations with N unknowns (the point sources), said equations being written to verify the conditions at the limits on the test points from the meshing.

II—Equating

Electromagnetic and Foucault Currents Case

Figure 3:
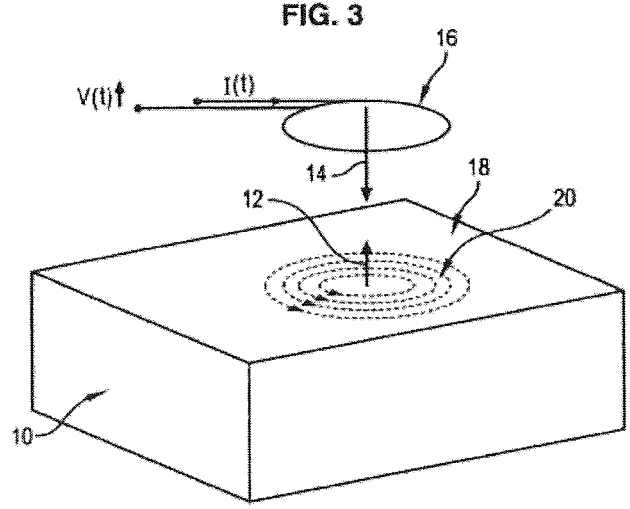
FIG. 3 is a three dimensional schematic view of an object subjected to an inductive electromagnetic field.
Figure 4:
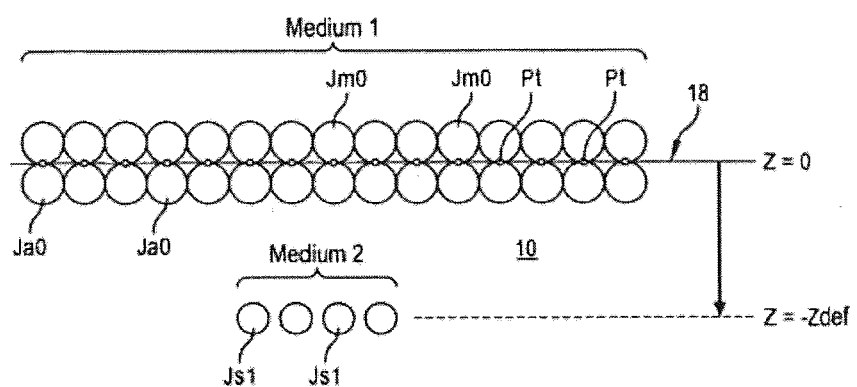
FIG. 4 is a sectional diagram illustrating the point sources in an object having a defect.

With reference to FIGS. 3 and 4, we are going to explain the equation serving as basis for the method according to the invention. In FIG. 3 is represented an object 10 that is, in the example that concerns us, electrically conductive and assimilated as semi infinite. A current loop 16 is positioned at a distance and facing an upper surface 18 of the object 10. This current loop 16 is supplied by an alternating electric current of voltage V(t) and intensity l(t), t being the time. The current loop 16 then generates towards the object 10 an inductive magnetic field 14. In response, the object 10 emits an induced magnetic field 12 and, at its upper surface 18, a Foucault current sheet 20. In FIG. 4, the schematic sectional view of the problem of FIG. 3 is represented: the plane Z=0 corresponds to the upper surface 18 of the tested object 10, an alternative field excitation device (here the current loop 16), situated in the environment or medium 1 (here the air) 'illuminates' the object 10, constituted here of the environment or medium 2, and creates within the sheets currents that decrease and dephase with the depth Z. A potential defect on the object 10 is situated, here, at a depth Z=−Zdef within the environment 2. As is explained in the documents WO2004/044790 and WO2007/071735, the DPSM method makes it possible to calculate the quantities associated with the different point sources Jm0, Ja0 and Js1, where:

- Jm0 are the point sources at the interface (which represents the surface 18) modelling the transmission of the quantities linked to the excitation device from the environment 1 to the environment 2,
- Ja0 are the point sources at the interface (which represents the surface 18) modelling the transmission of the quantities from environment 2 to environment 1,
- Js1 are the point sources associated with the potential defect on the object 10 modelling a perturbation of the quantities in the environment 2.

It should be recalled that the potential defect on the object is characterised by a local variation in the electrical properties (here the conductivity) and more generally the quantities associated with point sources.

Using the DPSM method applied to the situation illustrated in FIGS. 3 and 4, we can establish that the electric field $\vec{E}_1$ in the object 10, at a given depth Z1, is written:

$$\vec{E}_1 = Q_{1B} \cdot \vec{I}_B = Q_{10} \cdot \vec{J}_{M0}$$

Where $Q_{1B}$ is a matrix of coupling between the current sheet $\vec{I}_B$ of the excitation device at the current loop 16 and the points situated on the observation plane at depth Z1, and $Q_{10}$ is a matrix of coupling between the sheet of currents $\vec{J}_{M0}$ of the excitation device situated at Z=0 (sheet associated with point sources Jm0) and the points situated on the observation plane at depth Z1.

We deduce therefrom a value of the density of the currents in each of said points situated on the plane, by multiplying the field by the conductivity $\sigma_1$ at each point of said observation plane at depth Z1 ($\sigma_1$ is a diagonal matrix), and by assuming that the electric field is little affected by the presence of the potential defect on the object. The conductivity of the object without defect is $\sigma_0$:

$$\vec{J}_1 = \sigma_1 \cdot \vec{E}_1 = (\sigma_0 - \Delta\sigma_1) \cdot \vec{E}_1 \quad (2)$$

The perturbation currents are going to be defined from the perturbation of the conductivity $\Delta\sigma_1$ around $\sigma_0$, which is seen as the superposition of a density of perturbation currents $\vec{J}_{S1}$ with an initial current density without perturbation:

$$\vec{J}_{S1} = -\Delta\sigma_1 \cdot \vec{E}_1 \quad (3)$$

Figure 1:
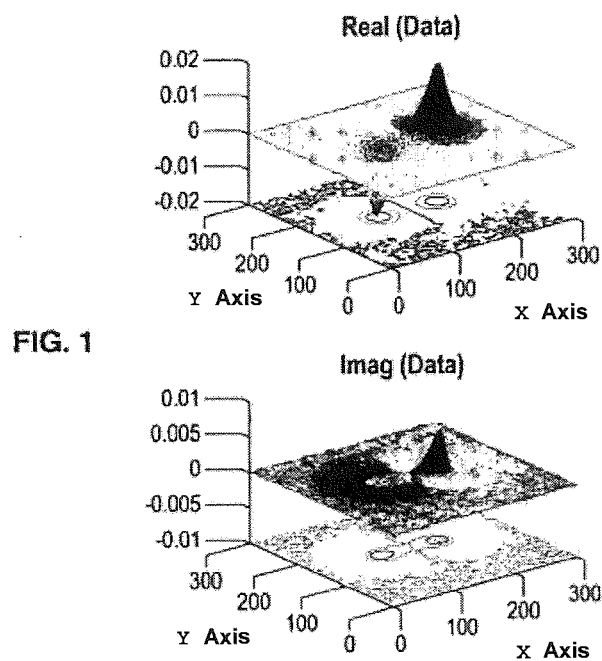
FIG. 1 is an image of a magnetic field measured at the surface of an object.
Figure 2:
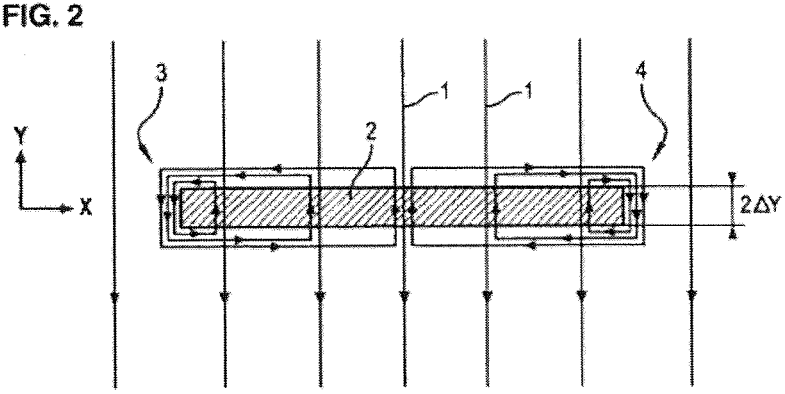
FIG. 2 is top view diagram of the object and the fields generated having led to the image of FIG. 1.

Thus, if we manage to find the density vector of perturbation currents $\vec{J}_{S1}$ corresponding then to the potential defect on the object and observed at the surface 18, we will indeed have a map of the variation in conductivity on said plane at depth Z1. The density of currents $\vec{J}_{S1}$ corresponds to the perturbation currents, corresponding in this particular case to the field 3 and 4 of FIG. 2.

We are now going to define a list of test points Pt situated at the surface 18 of the object 10 (at the contact points of the spheres containing the point sources Jm0 and Ja0), and measure the magnetic field at these points Pt. Jm0 are the point sources that radiate from the surface 18 (at Z=0) in the environment 2 of the object. Ja0 are the point sources that radiate from the surface 18 to the environment 1 situated above (here, the air). The continuity equations of each side 1 and 2 of the interface which represents the surface 18 are written:

$$\begin{cases} \vec{A}_1 = \vec{A}_2 \\ \frac{1}{\mu_1} \cdot \frac{\partial \vec{A}_1}{\partial \vec{n}} = \frac{1}{\mu_2} \cdot \frac{\partial \vec{A}_2}{\partial \vec{n}} \end{cases} \quad (4)$$

Where $\vec{A}_1$ and $\vec{A}_2$ are potential vectors at the points Pt, respectively in the environment 1 and in the environment 2, and $\mu_1$ and $\mu_2$, the respective permeability of the environments 1 and 2.

We recall that for the potential vector $\vec{A}$, in an orthonormed measurement:

$$\vec{A}x = \frac{\mu}{4\pi} \begin{bmatrix} \frac{e^{-jkR_{11}}}{R_{11}} & \cdots & \cdots & \frac{e^{-jkR_{1Ns}}}{R_{1Ns}} \\ \vdots & & & \vdots \\ \vdots & & & \vdots \\ \frac{e^{-jkR_{Np1}}}{R_{Np1}} & \cdots & \cdots & \frac{e^{-jkR_{NpNs}}}{R_{NpNs}} \end{bmatrix} \cdot \vec{J}x \Leftrightarrow \vec{A}x \quad (5)$$

$$= [Wxx] \cdot \vec{J}x$$

Where k is the wave number and $R_{nPnS}$ represents the distance between a source Ns and an observation point Np Thus $$\vec{A} = \begin{vmatrix} \vec{A}x \\ \vec{A}y \\ \vec{A}z \end{vmatrix} = \begin{bmatrix} Wxx & 0 & 0 \\ 0 & Wyy & 0 \\ 0 & 0 & Wzz \end{bmatrix} \cdot \begin{bmatrix} \vec{J}x \\ \vec{J}y \\ \vec{J}z \end{bmatrix} = W \cdot \vec{J} \quad (6)$$

For the derivative along the normal to the interface, in a point, we obtain:

$$\frac{\partial \vec{A}(\vec{r})}{\partial \vec{n}} = \begin{bmatrix} \frac{\partial Ax}{\partial x} & \frac{\partial Ax}{\partial y} & \frac{\partial Ax}{\partial z} \\ \frac{\partial Ay}{\partial x} & \frac{\partial Ay}{\partial y} & \frac{\partial Ay}{\partial z} \\ \frac{\partial Az}{\partial x} & \frac{\partial Az}{\partial y} & \frac{\partial Az}{\partial z} \end{bmatrix} \cdot \begin{bmatrix} n_x \\ n_y \\ n_z \end{bmatrix} \quad (7)$$

Since the normal is along the Z axis in this example:

$$\frac{\partial \vec{A}(\vec{r})}{\partial \vec{z}} = \begin{bmatrix} \frac{\partial Ax}{\partial x} & \frac{\partial Ax}{\partial y} & \frac{\partial Ax}{\partial z} \\ \frac{\partial Ay}{\partial x} & \frac{\partial Ay}{\partial y} & \frac{\partial Ay}{\partial z} \\ \frac{\partial Az}{\partial x} & \frac{\partial Az}{\partial y} & \frac{\partial Az}{\partial z} \end{bmatrix} \cdot \begin{bmatrix} 0 \\ 0 \\ 1 \end{bmatrix} \quad (8)$$

$$= \begin{bmatrix} \frac{\partial Ax}{\partial z} \\ \frac{\partial Ay}{\partial z} \\ \frac{\partial Az}{\partial z} \end{bmatrix}$$

$$= \sum_i \begin{vmatrix} \frac{\alpha_i \cdot \mu}{4\pi} \cdot [(z - Cz_i) \cdot Jx_i] \\ \frac{\alpha_i \cdot \mu}{4\pi} \cdot [(z - Cz_i) \cdot Jy_i] \\ \frac{\alpha_i \cdot \mu}{4\pi} \cdot [(z - Cz_i) \cdot Jz_i] \end{vmatrix}$$

Where $Cz_1$, is the coordinate along OZ of the point source i
And designating $$\frac{\partial \vec{A}(\vec{r})}{\partial \vec{n}} = \overrightarrow{dnA}(\vec{r})$$

and with $$\alpha_i = -\frac{e^{-jk \cdot R_i}}{R_i^2}\left[j \cdot k + \frac{1}{R_i}\right]$$

we obtain in matrix writing:

$$\overrightarrow{dnA} = \begin{vmatrix} \overrightarrow{dnA}x \\ \overrightarrow{dnA}y \\ \overrightarrow{dnA}z \end{vmatrix} = \begin{bmatrix} Yzx & 0 & 0 \\ 0 & Yzy & 0 \\ 0 & 0 & Yzz \end{bmatrix} \cdot \begin{bmatrix} \vec{Jx} \\ \vec{Jy} \\ \vec{Jz} \end{bmatrix} = Y \cdot \vec{J} \quad (9)$$

From this, the electric field $\vec{E}$ may be written $$\vec{E} = -\frac{\partial \vec{A}}{\partial t} = -j\omega \vec{A} \quad (10)$$

And the magnetic field $\vec{B}$ in a point:

$$\vec{B}(\vec{r}) = \sum_i \begin{vmatrix} \frac{\alpha_i \cdot \mu}{4\pi} \cdot [-(z - Cz_i) \cdot Jy_i + (y - Cy_i) \cdot Jz_i] \\ \frac{\alpha_i \cdot \mu}{4\pi} \cdot [-(x - Cx_i) \cdot Jz_i + (z - Cz_i) \cdot Jx_i] \\ \frac{\alpha_i \cdot \mu}{4\pi} \cdot [-(y - Cy_i) \cdot Jx_i + (x - Cx_i) \cdot Jy_i] \end{vmatrix} \quad (11)$$

I.e., in matrix writing:

$$\vec{B} = \begin{vmatrix} \vec{Bx} \\ \vec{By} \\ \vec{Bz} \end{vmatrix} = \begin{bmatrix} 0 & -Bzy & Byz \\ Bzx & 0 & -Bxz \\ -Byx & Bxy & 0 \end{bmatrix} \cdot \begin{bmatrix} \vec{Jx} \\ \vec{Jy} \\ \vec{Jz} \end{bmatrix} = X \cdot \vec{J} \quad (12)$$

The structures of these matrices provide information on the quantity to be measured: for example, if the orientation of the excitation current sheet is along the Y axis, thus that Jx and Jz are zero, it will only be possible to measure Bx and Bz, or uniquely the electric field Ey. This is very important because it makes it possible to understand and optimise the structure of the instrumentation.

From continuity equations (4), we develop the following matrix system:

$$\vec{C}_{OI} = \begin{bmatrix} \vec{H}_0 \\ \vec{0} \\ \vec{0} \end{bmatrix} \quad (13)$$

$$= \begin{bmatrix} 0 & 0 & M_{0A0} \\ W_{0S1} & +W_{0M0} & -W_{0A0} \\ 1/\mu_1 * Y_{0S1} & +1/\mu_1 * Y_{0M0} & -1/\mu_2 * Y_{0A0} \end{bmatrix} * \begin{bmatrix} \vec{J}_{S1} \\ \vec{J}_{M0} \\ \vec{J}_{A0} \end{bmatrix}$$

$$= T_1 \cdot \vec{J}_1$$

In which the matrices W calculate the potential vector A at the test points Pt situated at the surface 18, at Z=0. The matrices Y calculate the derivative along the normal to the surface 18 of the potential vector at the same points, and the matrix M calculates the components of the field H at these points. Then, by inversion of this relation, we can find the complete list of point sources J (Jm0, Ja0 and Js1) because H is known by the measurement on the surface 18 of the object 10. The field H measured at the surface is either the magnetic field B, or the electric field E. The coupling matrix T is developed from the matrices M, W and Y. It is an inversible matrix.

By analytically resolving the matrix system (13), all calculations made, this gives:

$$\vec{H}_0 = M_{0A0} \cdot (W_{0M0}^{-1} * W_{0A0} - Y_{0M0}^{-1} * Y_{0A0})^{-1} * (W_{0M0}^{-1} * W_{0S1} - Y_{0M0}^{-1} * Y_{0S3}) * \vec{J}_{S1} = M_{0S1eq} * \vec{J}_{S3} \quad (13')$$

In practice and in a general manner, the method for quantitatively estimating defects present in an object comprises the following steps:

a) "illuminating" a surface of the object with an inductive wave field, particularly an electromagnetic or ultrasound field, etc.

b) measuring, at the surface of the object, an induced wave field $\vec{C}_{p1}$ using a measuring device. The resolution of the measurement device indicates the maximum meshing that can be considered for the DPSM method that enables the matrix system (13) to be developed c) developing a coupling matrix $T_1$ from the properties of the material of the object d) solving the matrix system (13) in order to determine the vector $\vec{J}_1$, at depth Z1 e) extracting the sub-vector $\vec{J}_{S1}$ corresponding to a potential defect on the object at depth Z1 f) quantitatively estimating the potential defect from the sub-vector $\vec{J}_n$ at depth Z1.

In order to estimate in three dimensions the potential defect, it suffices to repeat the preceding steps for different depths Z.

We are going to illustrate hereafter the method according to the invention by an example.

III—Application Example

Currents Equivalent to Cracks

In this example of the method according to the invention, we are going to illustrate an application of this method according to the invention within the context of an inductive magnetic field and Foucault currents. To do this, we are going to estimate with the method according to the invention, at different depths Z of the object, the current sheets Js that synthesise the field measured at the potential defect present in said object.

For more simplicity in the description, and to show the robustness of the method according to the invention, we are going to ignore the role of the interface. To do this, we have seen that the equation (13') makes it possible to calculate the field $\vec{H}_{0+}$ at Z=0+ (in the environment 1, just above the surface 18). There exists another equation that enables the direct calculation of the field $\vec{H}_{0-}$ at Z=0- (in the environment 2, just below the surface 18): in the case where only the normal component of the induced wave field, which is continuous at the crossing of the interface, is measured, and that the materials present are non-magnetic, we can assimilate $\vec{H}_{0+}=\vec{H}_{0-}$ and directly write that:

$$\vec{H}_0 = M_{0S1} \cdot \vec{J}_{S1} \qquad (14)$$

This equation will be called hereafter observation equation.

The density of perturbation currents, $\vec{J}_{S1} = -\Delta\sigma_1 \cdot \vec{E}_1$ that results thereof and which appears in the model from the DPSM method, is multiplied by the frontal surface of the defect: $\Delta S = \Delta X \cdot \Delta Z$ and by $\Delta y$ which is the meshing step (it should be recalled that the currents Js are homogeneous with Ampere.meters). We thus have the height $\Delta Z$ of the defect in each mesh of step $\Delta X \Delta Y$:

$$\vec{J}_{S1}DPSM = \Delta S \cdot \Delta Y \cdot (-\Delta\sigma_1 \cdot \vec{E}_1) \qquad (15)$$

The term $\Delta S \cdot \Delta Y$ represents the volume of the elementary voxel. In the remainder of the description, we will merge $\vec{J}_{Sk}$ DPSM with $\vec{J}_{S1}$ for greater writing simplicity.

FIGS. 5 to 8 illustrate some results ob $$\vec{H}_0 = M_{0S1} \cdot \vec{J}_{S1}$$

(FIGS. 5 and 6) and parallel (FIGS. 7 and 8) to the excitation current sheet) in an object 10, with a device (ECI imager) that only measures the component Hz of the induced field at the surface, and an excitation sheet from the inductive field oriented along the axis OY.

Figure 5:
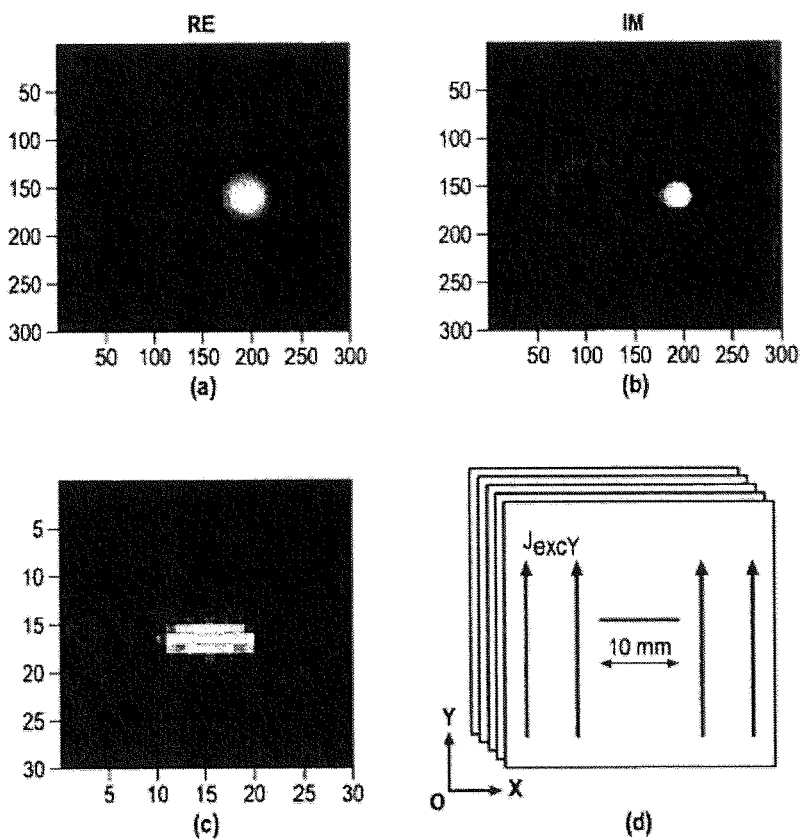
FIGS. 5 to 8 illustrate examples obtained using a method according to the invention

FIG. 5 illustrates the field Hz [(a): real part, (b) imaginary part] measured by the ECI imager for an excitation of 1600 Hz, for a defect of emerging crack type oriented along Ox (length, opening, depth of the crack=10×0.1×1.2 mm) in a stacking of metal sheets 2017A (formerly AU4G) on a surface of 30×30 mm forming the object 10 (d), and estimation by the method according to the invention of the equivalent DPSM sheet at a depth Z=0.5 mm (c). It should be noted that the field images have, here, a spatial resolution of 0.1×0.1 mm, the images of the DPSM sheets have a resolution of 1×1 mm (dimensioning of the meshing), for practical implementation reasons. It is possible to have a meshing in which the dimensioning corresponds to the resolution of the field images effectively measured by the ECI imager. In the case illustrated, this resolution has been lowered by grouping together sets of 10 pixels by 10 pixels of the field images, the values of which have been averaged before resolving the matrix system (14).

Figure 6:
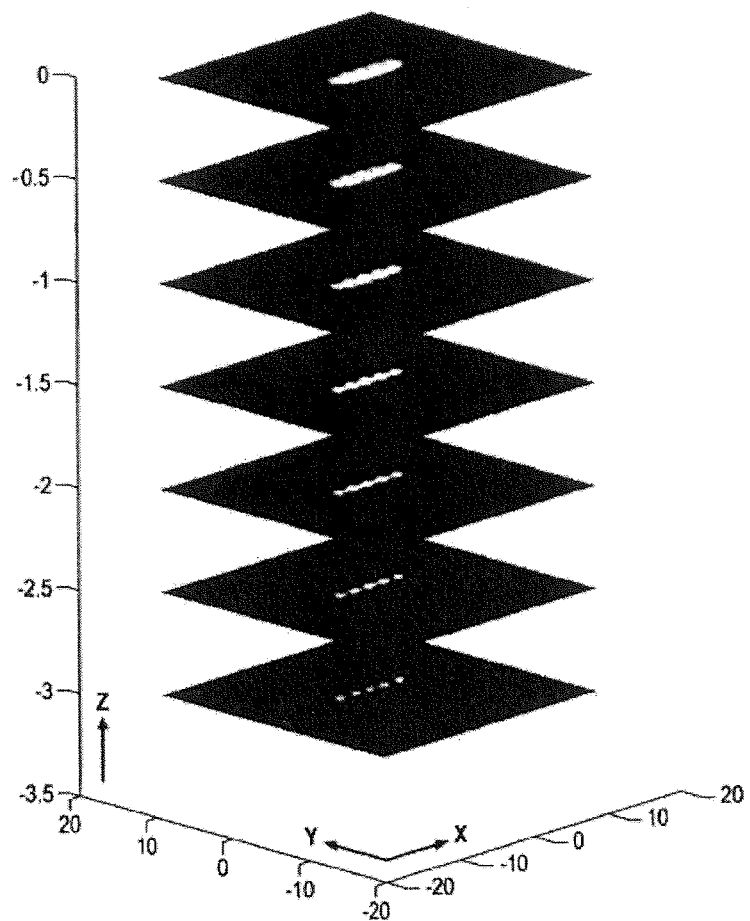

FIG. 6 illustrates the result of the method according to the invention for the estimation of the DPSM current sheets, between 0 and 3.5 mm depth, for the defect (oriented along Ox) of FIG. 5.

Figure 7:
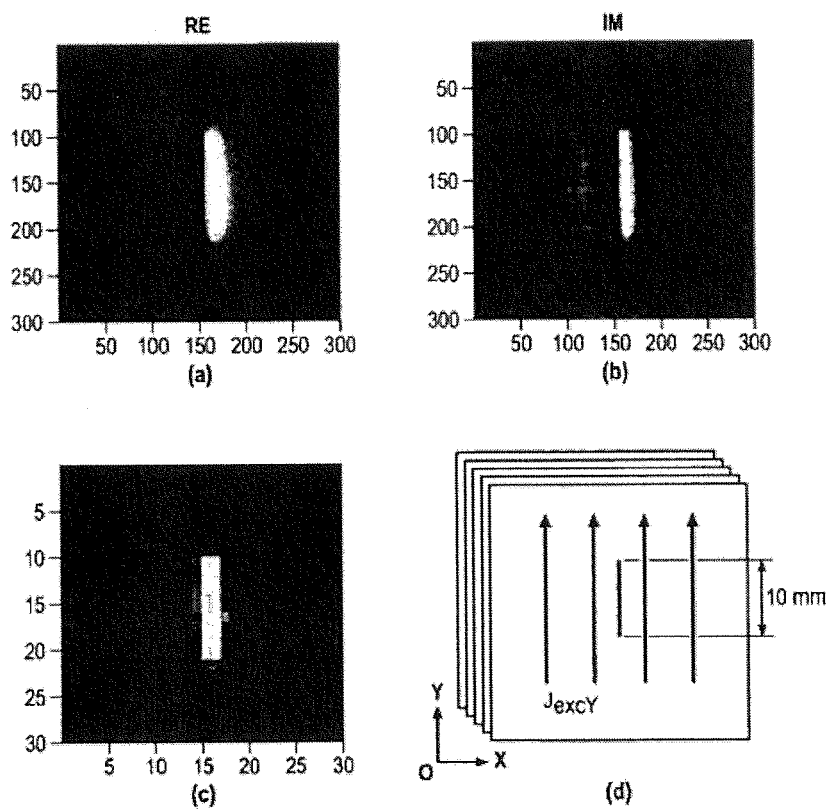

FIG. 7 illustrates the field Hz [(a): real part, (b): imaginary part] measured by the ECI imager for an excitation of 1600 Hz, for a defect of emerging crack type oriented along Oy (length, opening, depth of the crack=10×0.1×1.2 mm) in a stacking of metal sheets 2017A (formerly AU4G) on a surface of 30×30 mm forming the object 10 (d), and estimation by the method according to the invention of the DPSM sheet equivalent to a depth Z=0.5 mm (c). As previously, it should be noted that the field images have, here, a spatial resolution of 0.1×0.1 mm, the images of the DPSM sheets have a resolution of 1×1 mm (dimensioning of the meshing), for practical implementation reasons. It is possible to have a meshing in which the dimensioning corresponds to the resolution of the field effectively measured by the ECI imager. In the case illustrated, this resolution has been lowered by grouping together sets of 10 pixels by 10 pixels of the field images of which the values have been averaged before resolving the matrix system (14).

Figure 8:
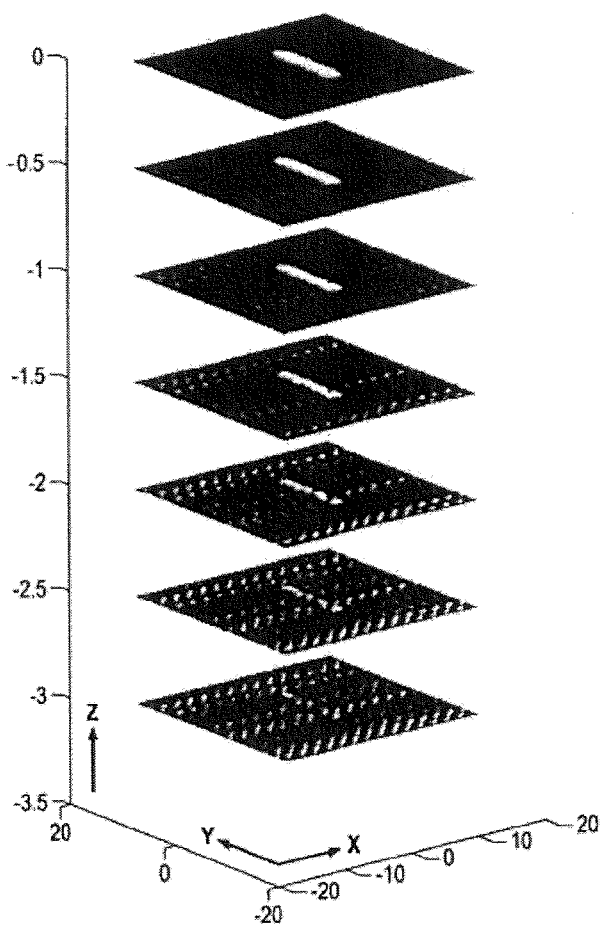

FIG. 8 illustrates the result of the method according to the invention for the estimation of the DPSM current sheets, between 0 and 3.5 mm depth, for the defect (oriented along Oy) of FIG. 7.

IV—First Evolution

Sorting of Currents by Sheet at Depth

In the preceding chapter, the concepts of perturbation currents were validated, since we note that the inversion of the DPSM matrix of F coupling indeed gives a current sheet concentrated Js in the defect, and of opposite sense to that of the excitation (see FIGS. 5, 6, 7 and 8).

Figure 9:
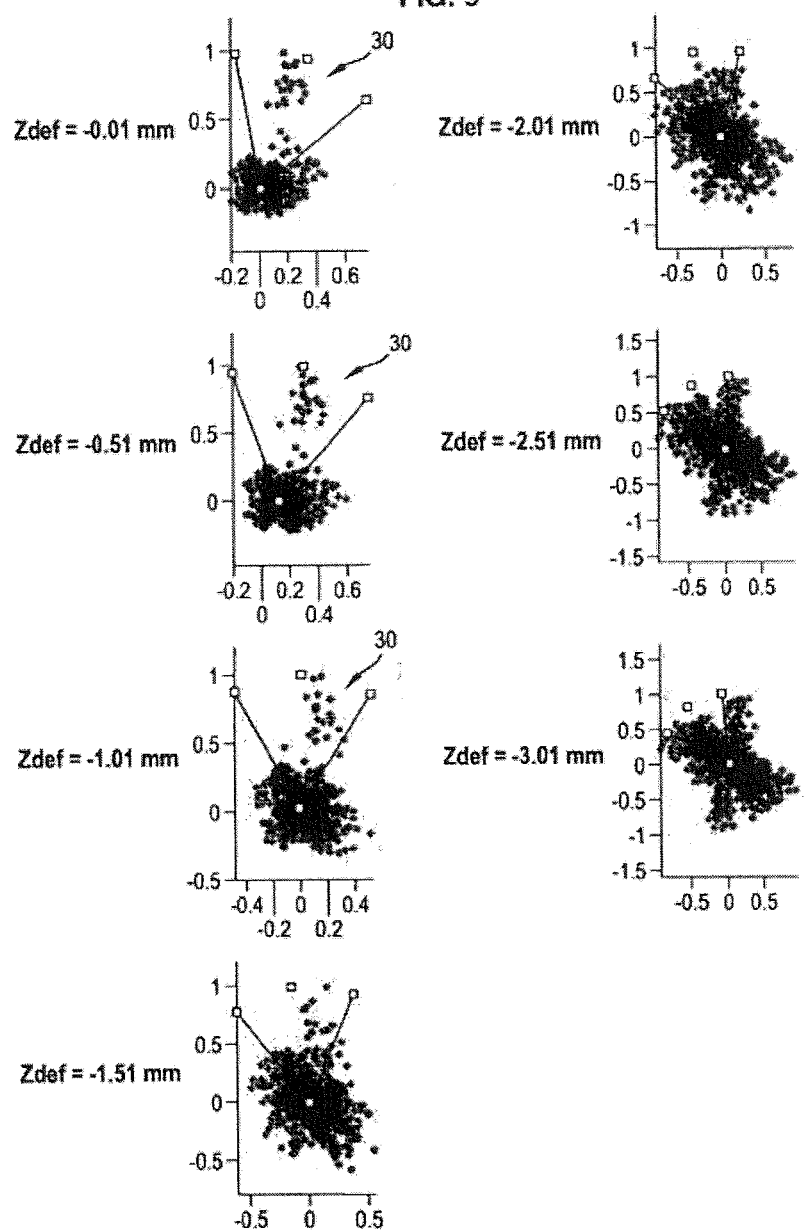
FIG. 9 illustrates a screening introduced in the method according to the invention.
Figure 10:
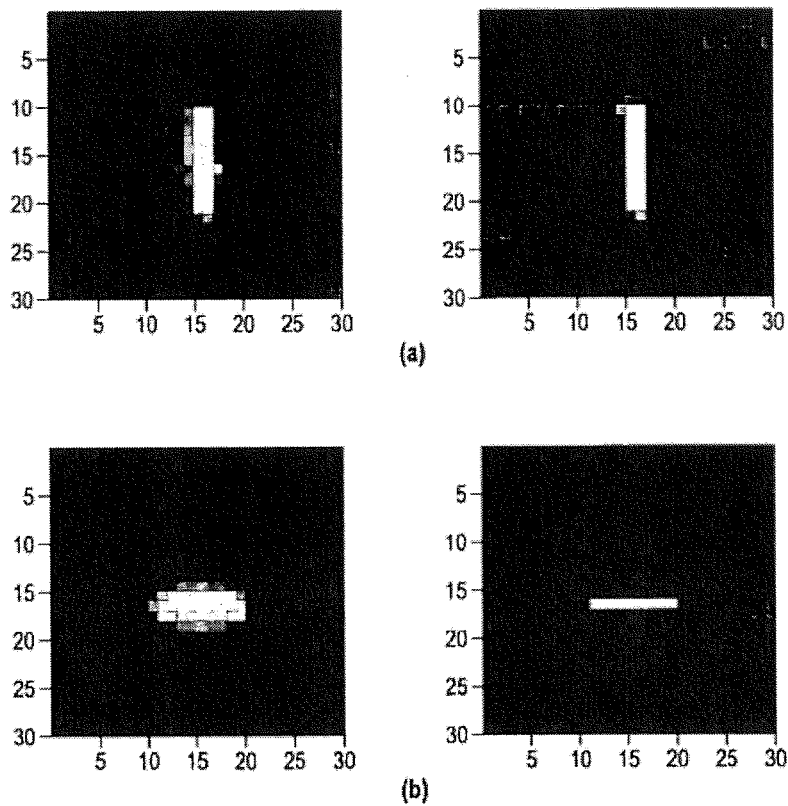
FIGS. 10 and 11 illustrate an example of result obtained using the screening of FIG. 9.

Nevertheless, the precision is not sufficient to characterise the defect. Since it is necessary each time to inverse the equivalent matrix $M_{OS_{eq}}$ of the equation (13') to obtain the potential defect at depth Z1, and that the measurement of induced wave field at the surface 18 generates noise, it is desirable to regularise the matrix equivalent during its inversion. To do this, we are going to take into account information a priori on the excitation currents. In fact, the examples of FIGS. 6 and 8 show that on the DPSM current sheets estimated for depths beyond Z=−1.5 mm, the defect is always present whereas the latter is in fact at 1.2 mm depth. The idea is now to look at the DPSM current sheets at different depths and to only keep the estimated currents in which the phase and module are in harmony with those of the excitation currents at given depth. We call this operation "screening". FIG. 9 illustrates an example taken on the emerging crack oriented along Oy of FIG. 7. Said FIG. 9 represents clouds of points in the complex plane, for each of the estimated DPSM current sheets, as a function of the depth. The points in the angular sector 30 correspond to the points selected by screening in amplitude and in phase. FIG. 10 illustrates the application of said screening for a DPSM current sheet estimated at depth 0.5 mm before (on the left) and after screening (on the right), for the defects along Ox (a) and along Oy (b).

Figure 11:
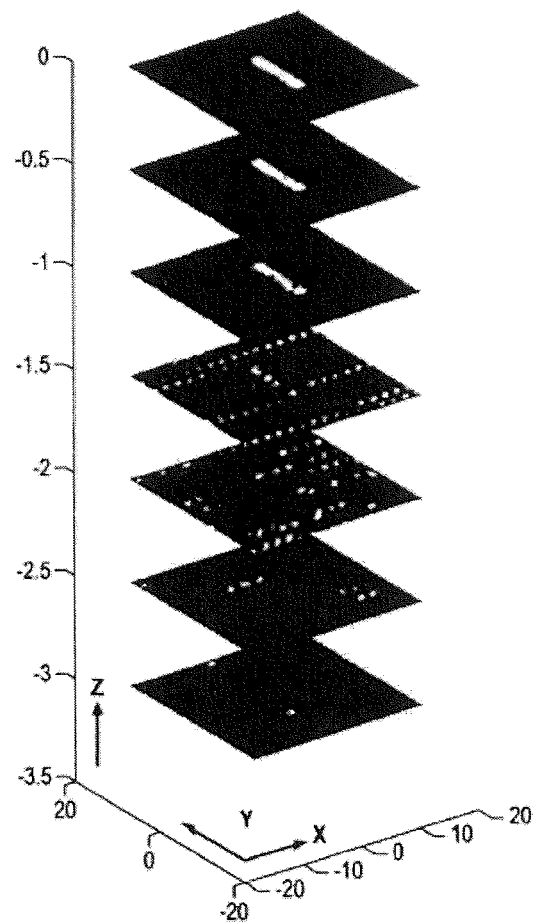

FIG. 11 illustrates an example of screening included in the method according to the invention which enables the estimation of DPSM current sheets, between 0 and 3.5 mm depth, for the defect (oriented along Oy) of FIG. 7, after operation of screening in module and in phase, as a function of their concordance with excitation sheets of the applied inductive field. The real depth of the defect is 1.2 mm.

V—Second Evolution

Progressive Screening (Iterative)

Progressive screening consists in estimating the DSPM current sources of the layer p at a given depth Zp, while taking into account the current sheets estimated in the preceding layer p−1 at a depth Zp−1. To implement this iterative approach, the method according to the invention subtracts at each iteration p all or part of the measured mapping $\vec{H}_Z'(Z_{p-1})$ field which could be due uniquely to the sources estimated and screened in the preceding layer p−1, from the measured mapping of the considered field $\vec{H}_s^{mesuré}(Z_p)$. The sources of layer currents of depth Zp are thus estimated at the iteration p from the field mapping:

$$\vec{H}_Z(Z_p) = \vec{H}_Z^{mesuré}(Z_p) - K \cdot \vec{H}_Z'(Z_{p-1}) \quad (16)$$

in which K is a "reinjection" coefficient that can vary from 0 (no progressive screening) to 1 (progressive screening).

First hypothesis—"the hollow punch": the sources of DSPM currents corresponding to the defect are virtual sources that cancel out, in the defect, the Foucault currents induced in the material. Said sources are then considered as radiating in the material of the object. Consequently, then comprises said sources of the layer p−1 and will be subtracted from the measured mapping of the layer p.

Figure 12:
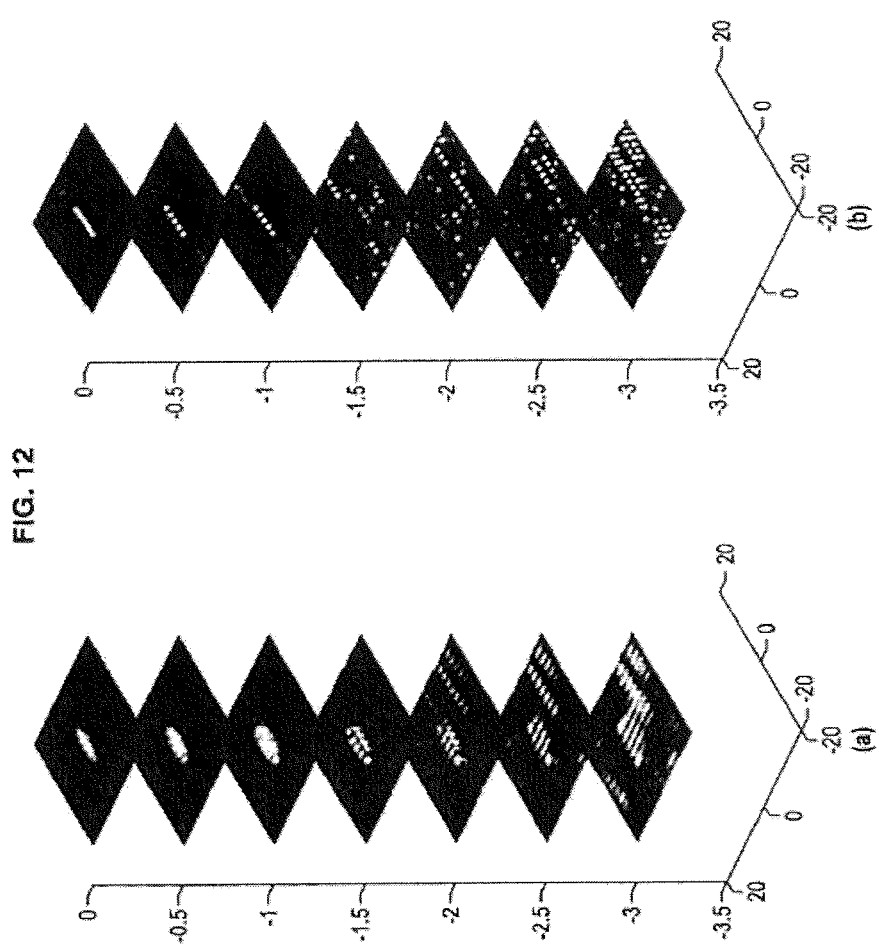
FIGS. 12 to 15 illustrate examples of progressive screening introduced in the method according to the invention.

FIG. 12 illustrates a reconstruction by the method according to the invention of DPSM current sheets, by progressive screening with K=0.3, on the left (a) before screening, on the right (b) after screening. The defect has a real depth of 1.2 mm. It is oriented along Ox and the excitation current sheet is along Oy (FIG. 5).

Figure 13:
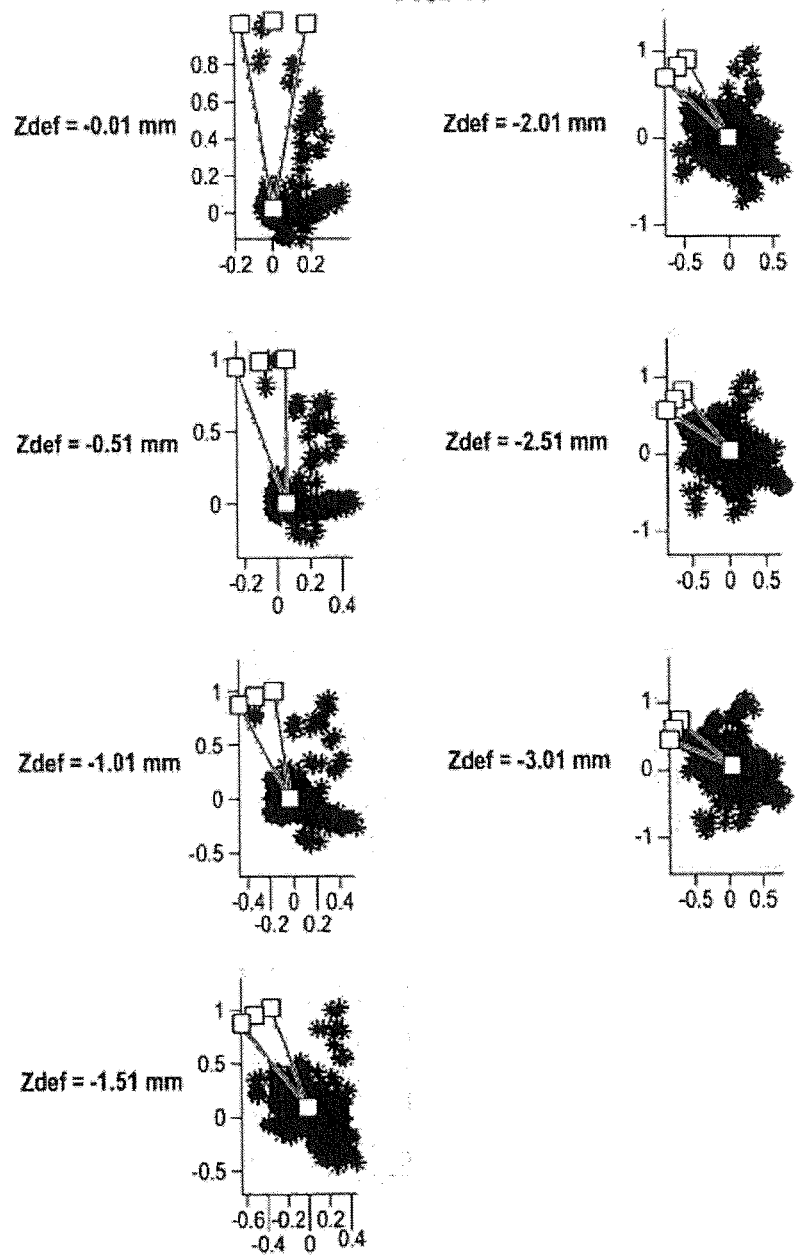

FIG. 13, for its part, shows the screening used (the angular section of screening corresponds to the de-phasing dphi of the excitation wave in the considered depth dZ (here dZ=0.5 mm at 1600 Hz, and dphi=10°).

Figure 14:
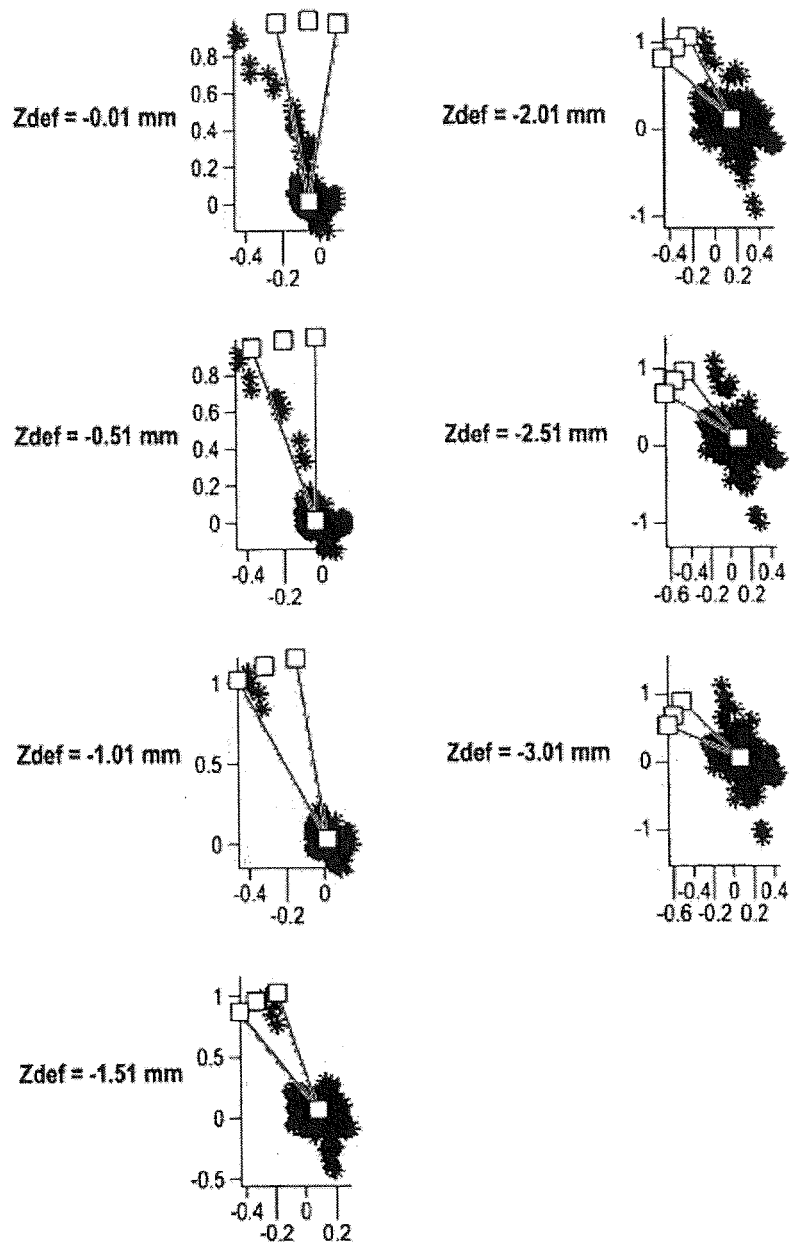
Figure 15:
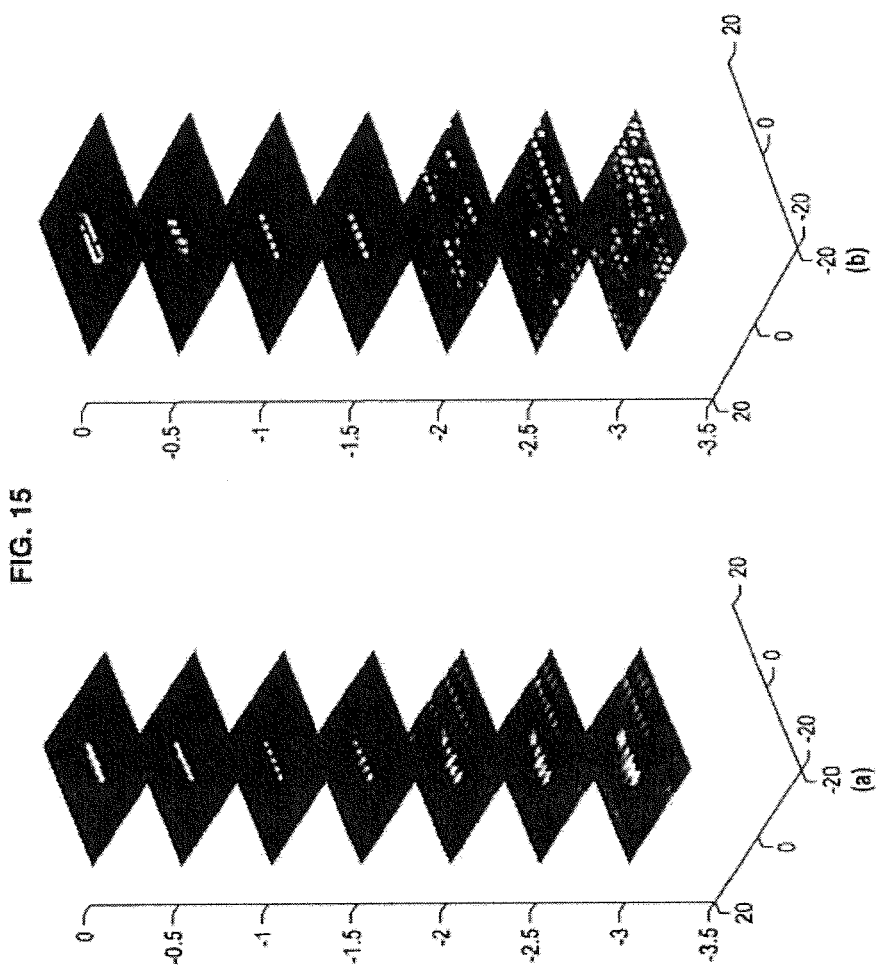

Second hypothesis: we will now consider a new working hypothesis: the DSPM sources correspond to the currents, still oriented along the axis Oy, which appear at the "edges" of the defect, in other words around the walls and under the defect. These sources are selected to form $\vec{H}_z'(Z_{p-1})$. Said currents correspond to the excitation currents that are deviated around and under the defect. According to this hypothesis, the magnetic field of reaction due to the circulation of said "defect" currents propagates in the air (in other words in the volume of air of the defect). We thus take into account this new hypothesis in the progressive screening to estimate with the method according to the invention, at each iteration, the contributions of the magnetic field of reaction due to the current sources at the edges of the defect. We then obtain the results of FIG. 15 (reconstruction of the DPSM current sheets "at the edges" of the defect, by progressive screening with K=0.3, on the left (a) before screening, on the right (b) after screening. Real depth of the defect: 1.2 mm, defect oriented along Ox and excitation current sheet along Oy), with the screening of FIG. 14 (screening used (the angular sector of screening corresponds to the de-phasing dphi of the excitation wave in the considered depth dZ (here dZ=0.5 mm at 1600 Hz, and dphi=10°).

It should be noted that, after screening, the presence of currents Jy "around" the defect at the surface, and currents flowing "under" the defect in layer Z=1.5 mm.

VI—Third Evolution

Global Multifrequency Formulation

Still to improve the precision of the estimation of the defect In the object, the idea now is to find a global formulation to take account of an "enrichment" of the available signal by having available a range of excitation frequencies.

To do this, we are going to write the observation equation at different frequencies and by considering simultaneously the contribution of several layers of DPSM current sheets at different depths.

At a depth $Z_1$ and for an excitation frequency $F_1$, the excitation equation may be written, for an excitation current $I_0$ of frequency $F_1$ situated at the surface, the equation:

$$\vec{E}_1 = Q_{10} \cdot \vec{J}_{M0}$$

rewritten $\vec{E}_1^{F1} = Q_{10}^{F1} \cdot \vec{J}_{M0}^{F1}$

A perturbation current density ensues:

$$\vec{J}^{F1}_{S1} = \Delta S \cdot \Delta Y \cdot (-\Delta \sigma_1 \cdot \vec{E}^{F1}_1) \quad (18)$$

The measured field H is expressed by the observation equation, in Z=0, seen previously:

$$\vec{H}^{F1}_0 = M^{F1}_{0S1} \cdot \vec{J}^{F1}_{S1} = M^{F1}_{0S1} \cdot \Delta \sigma_1 \cdot Q_{10}^{F1} \cdot \vec{J}_{M0}^{F1} \quad (19)$$

Equation which is written more simply in the form, for the layer of depth $Z_1$ and frequency $F_1$:

$$\vec{H}_{F1} = M_{11} \cdot \vec{J}_{S11} = M_{11} \cdot \Delta \sigma_1 \cdot Q_{11} \cdot \vec{J}_{M31} \quad (20)$$

It may be seen that if $\vec{J}_{S11}$ depends on the frequency, $\Delta \sigma_1$ does not depend on it, and since $\Delta \sigma_1$ is a diagonal matrix and $Q_{11} \vec{J}_{M31}$ a column vector, the equation (2) is written:

$$\vec{H}_{F1} = M_{11} \cdot \vec{J}_{S11} = M_{11} \cdot \text{diag}(Q_{11} \cdot \vec{J}_{M01}) \cdot \Delta \sigma_1 \quad (21)$$

For three frequencies for example and from the preceding relation (15), the following matrix writing is deduced there from:

$$\begin{bmatrix} \vec{H}_{F1} \\ \vec{H}_{F2} \\ \vec{H}_{F3} \end{bmatrix} = \Delta V \cdot \begin{bmatrix} M_{11} \cdot \text{diag}(Q_{11} \cdot \vec{J}_{M01}) & M_{12} \cdot \text{diag}(Q_{21} \cdot \vec{J}_{M01}) & M_{13} \cdot \text{diag}(Q_{31} \cdot \vec{J}_{M01}) \\ M_{21} \cdot \text{diag}(Q_{12} \cdot \vec{J}_{M02}) & M_{22} \cdot \text{diag}(Q_{22} \cdot \vec{J}_{M02}) & M_{23} \cdot \text{diag}(Q_{32} \cdot \vec{J}_{M02}) \\ M_{31} \cdot \text{diag}(Q_{13} \cdot \vec{J}_{M03}) & M_{32} \cdot \text{diag}(Q_{23} \cdot \vec{J}_{M03}) & M_{33} \cdot \text{diag}(Q_{33} \cdot \vec{J}_{M03}) \end{bmatrix} * \begin{bmatrix} \vec{\sigma}_1 \\ \vec{\sigma}_2 \\ \vec{\sigma}_3 \end{bmatrix} \quad (22)$$

Where $\Delta V$ is the voxel considered in the analysed object.

Observation:

We note that the more the index of the column increases, the more the path in the material increases and the more the attenuation increases. Similarly, the more the index of the line increases, the more the frequency diminishes (by convention) and the lower the attenuation as a function of the depth in the material. Thus, if the staging of the frequencies is such that the first line only conserves the first term (this is a little caricatured, but quite realistic), the second line the two first terms, etc., a well-conditioned lower triangular matrix will be obtained. It will have the appearance of an integration matrix and will be easy to inverse to recover the layers of values of $\sigma(x, y)$ at each depth Z and thereby reconstruct an image close to the real form of the defect.

This is made possible by the calculation speed of the method, compatible with real time and thus exploitation by an operator in NDC. We are going to see in the following paragraph that the information can be enriched and try to access several information cueson the content of each voxel discretising the object thus analysed.

Illustration:

In the following example, we will look at a volumic defect of lack of material type, which extends over three layers in a conductive environment (aluminium alloy), according to FIG. 16.

Figure 17:
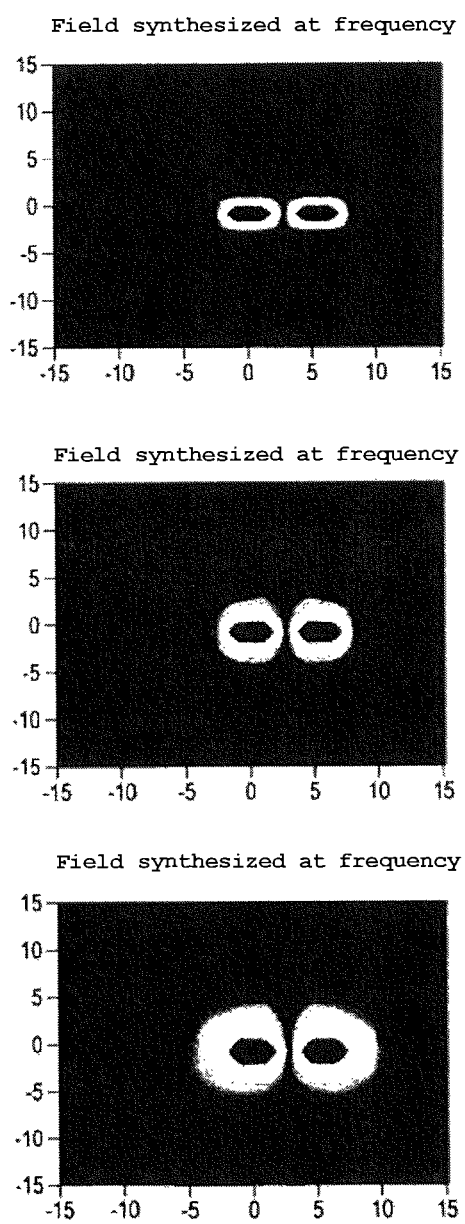

The distribution of the normal magnetic field resulting at the surface of the interaction of the wave emitted by the ECI with the complex defect is calculated by the DPSM method at three frequencies f1 (here 100 kHz), f2 (here 10 kHz) and f3 (here 1 kHz) and represented in module in FIG. 17.

Figure 16:
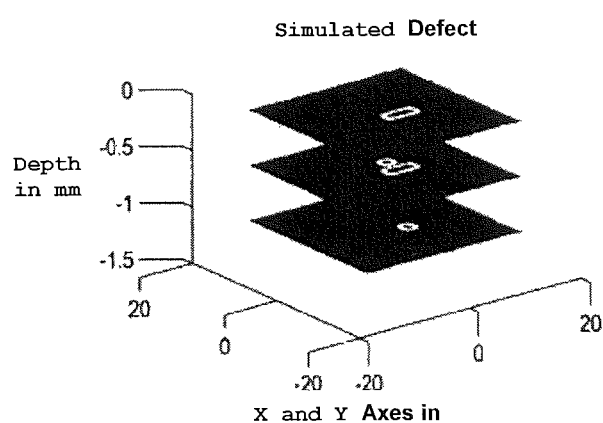
Figure 18:
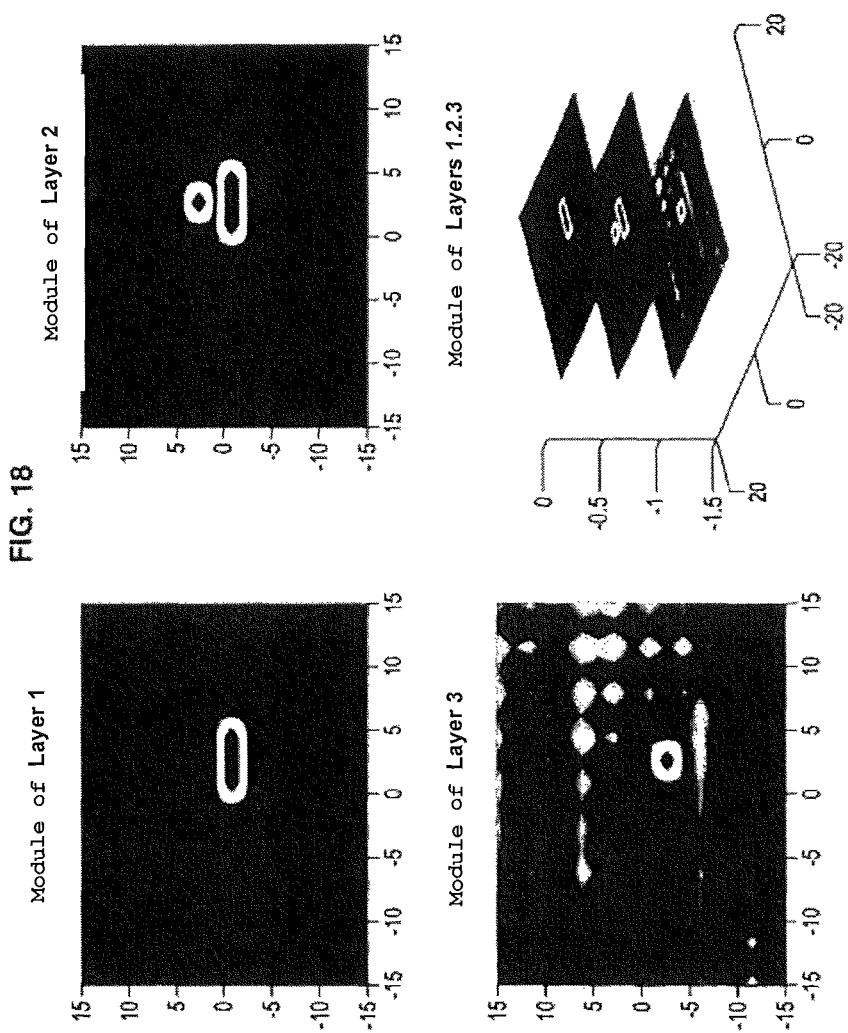
Figure 19:
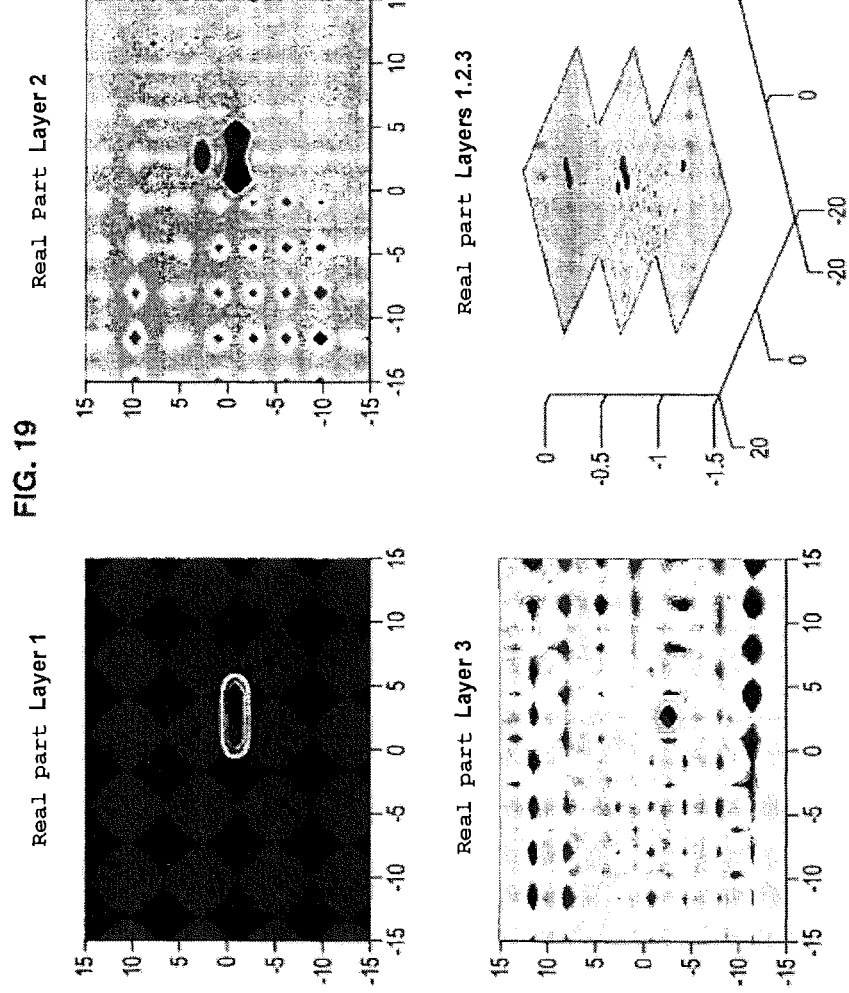

The implementation of the multi-frequency inversion technique presented above enables the following estimations of DPSM current sheets to be obtained:

In the case of field images having a favourable signal to noise ratio (64 dB): the three layers of the defect of FIG. 16 are correctly estimated (FIG. 18), while the estimation made using the frequencies f1, f2 and f3 exploited in isolation give less relevant results for the deepest layers (FIG. 19).

Figure 22:
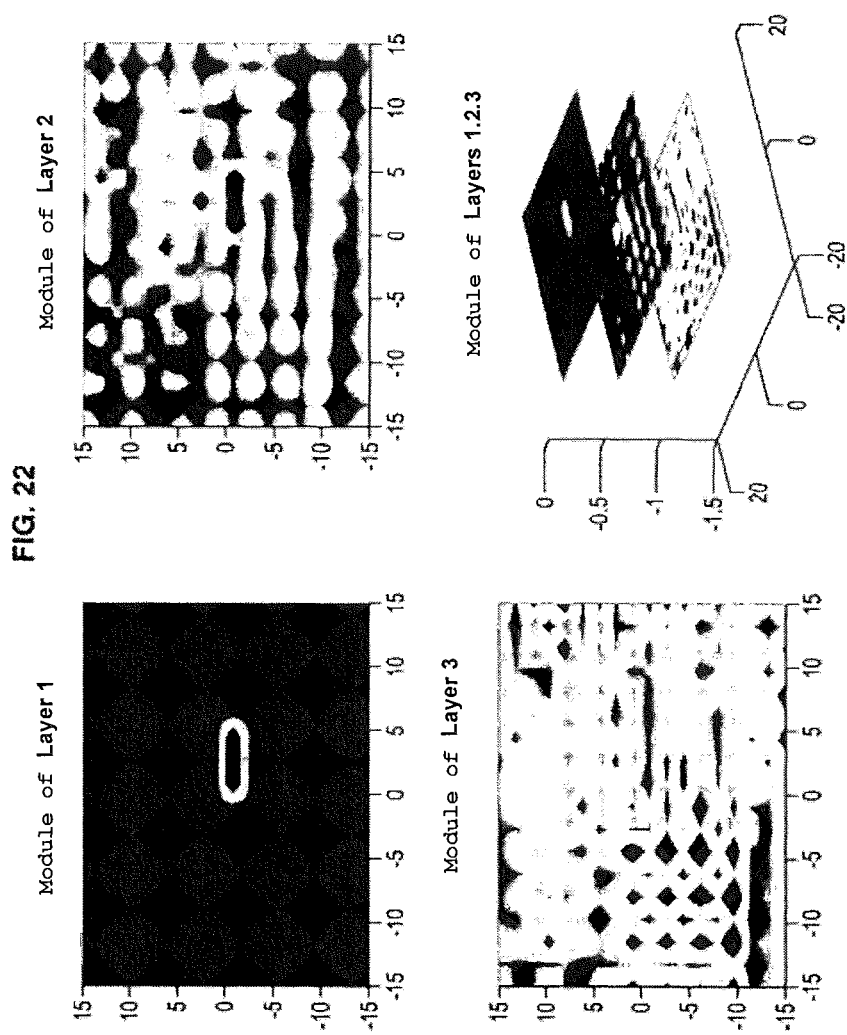

In the case of field images having a more unfavourable signal to noise ratio (44 dB): the multi-frequency estimation results are presented in the figures in real part (FIG. 20), imaginary (FIG. 21) and in module (FIG. 22).

The results presented above may be improved by refining the discretisation (meshing) of the study domain, limited for practical reasons to 18×18 pixels per layer. These results need to be compared to those obtained in the same conditions but using a single observation frequency (FIG. 23: estimation of the DPSM layers relative to the defect, after mono-frequency inversion at f1=100 kHz, then f2=10 kHz then f3=1 kHz for the defect of FIG. 16, from synthetic field images of signal to noise ratio 44 dB).

These results validate the feasibility and the interest of the multifrequency approach of the estimation of layers of DPSM current sheets for an improvement of the characterisation of complex defects.

VII—Fourth Evolution

Rotating Field

In fact, in the preceding expression (22), the values of σi that compose the vector $\vec{\sigma}_1$, for example, are considered as constant in the voxel $\Delta V = \Delta X \cdot \Delta Y \cdot \Delta Z$.

If we look more closely at this equation, we see that in the considered voxel, around the depth $Z_1$ $Z_2$, or $Z_3$, $\sigma_i$ is written rather as a volumic integral:

$$\sigma_i = \frac{1}{\Delta X \Delta Y \Delta Z} \cdot \int_{-\Delta X/2}^{+\Delta X/2} \int_{-\Delta Y/2}^{+\Delta Y/2} \int_{-\Delta Z/2}^{+\Delta Z/2} \sigma(x, y, z) \cdot dx \cdot dy \cdot dz \quad (23)$$

It should be noted that this writing incorporates the volume of the voxel ΔV that appears in the preceding general matrix equation (22). If the conductivity only evolves in a slow manner within the voxel and from one voxel to the next, it is possible to merge σ(x,y,z) with σi, which becomes the average volumic value of σ(x,y,z) in the considered voxel.

Figure 24:
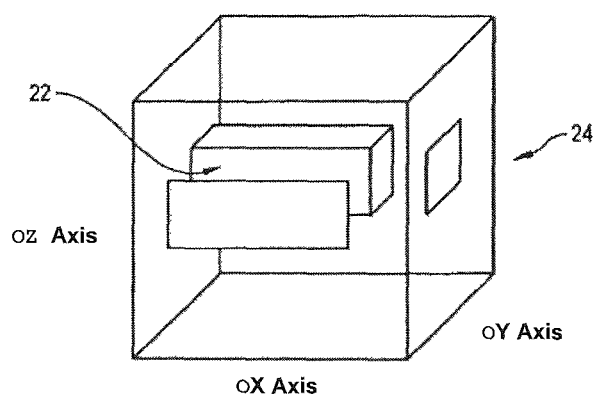
FIG. 24 is a three dimensional schematic view illustrating a voxel comprising a defect.

If the variation is sudden (presence of a crack for example), then it is advisable to examine the problem differently. On the one hand, if there are only two values taken by the variation din conductivity $\sigma_i$, namely 0 or $\sigma_0$, $\sigma_i$ is written:

$$\sigma_i = \frac{1}{\Delta X \Delta Y \Delta Z} \cdot \int_{-\Delta X/2}^{+\Delta X/2} \int_{-\Delta Y/2}^{+\Delta Y/2} \int_{-\Delta Z/2}^{+\Delta Z/2} \sigma(x, y, z) \cdot dx \cdot dy \cdot dz = \frac{\sigma_0 \cdot dv}{\Delta V} \quad (24)$$

dv=dx·dy·dz is the volume of the defect (22, FIG. 24) situated within the voxel ΔV (24, FIG. 24).

Furthermore, in a ECI Foucault current device, the perception of the defect will be made essentially on the surface perpendicular to the induced currents, the information being proportional to the surface projected on this plane: green surface if the excitation currents are oriented along the axis OX, blue surface in the other cases (axis OY).

Consequently, the signal collected leading to the estimation of the variation in conductivity in the pixel will take the following form:

Excitation along the axis OY: we 'see' the maximal section corresponding to a given Y, signal little dependent on the real 'depth' of the defect along OY:

$$\sigma_{iXoZ} = \frac{1}{\Delta X \Delta Y \Delta Z} \cdot \int_{-\Delta X/2}^{+\Delta X/2} \int_{-\Delta Z/2}^{+\Delta Z/2} \sigma(x, y, z) \cdot dx \cdot dz \quad (25)$$

$$= \Delta Y \cdot \frac{\sigma_0 \cdot dx \cdot dz}{\Delta V}$$

$$= \frac{\sigma_0 \cdot dx \cdot dz}{\Delta X \cdot \Delta Z}$$

Excitation along the axis OX: we 'see' the maximal section corresponding to a given X, signal little dependent on the real 'depth' of the defect along OX:

$$\sigma_{iYoZ} = \frac{1}{\Delta X \Delta Y \Delta Z} \cdot \int_{-\Delta Y/2}^{+\Delta Y/2} \int_{-\Delta Z/2}^{+\Delta Z/2} \sigma(x, y, z) \cdot dy \cdot dz \quad (26)$$

$$= \Delta X \cdot \frac{\sigma_0 \cdot dy \cdot dz}{\Delta V}$$

$$= \frac{\sigma_0 \cdot dy \cdot dz}{\Delta Y \cdot \Delta Z}$$

We can see that if we wish to reconstitute the exact geometry of the object within the voxel, at least one equation is lacking, because it is necessary to estimate dx, dy, and dz.

Figure 25:
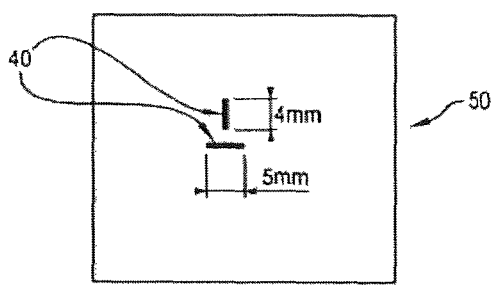
FIG. 25 is a top view of a thick solid plate comprising a "T" shaped crack.

Illustration:

FIG. 25 shows an image of a 'T-shaped' crack 40 in a solid, thick (20 mm) plate 50 made of Inconel (conductivity 1 MS/m). The depth of the defect is 1 mm, and the openings are 1 mm: if we consider that dz is known (and for example equal or fixed by convention to ΔZ), then it is possible to recover, according to the two preceding expressions (25 and (26), the values of dx and dy by creating an excitation respectively along the axes OY and OX.

Figure 26:
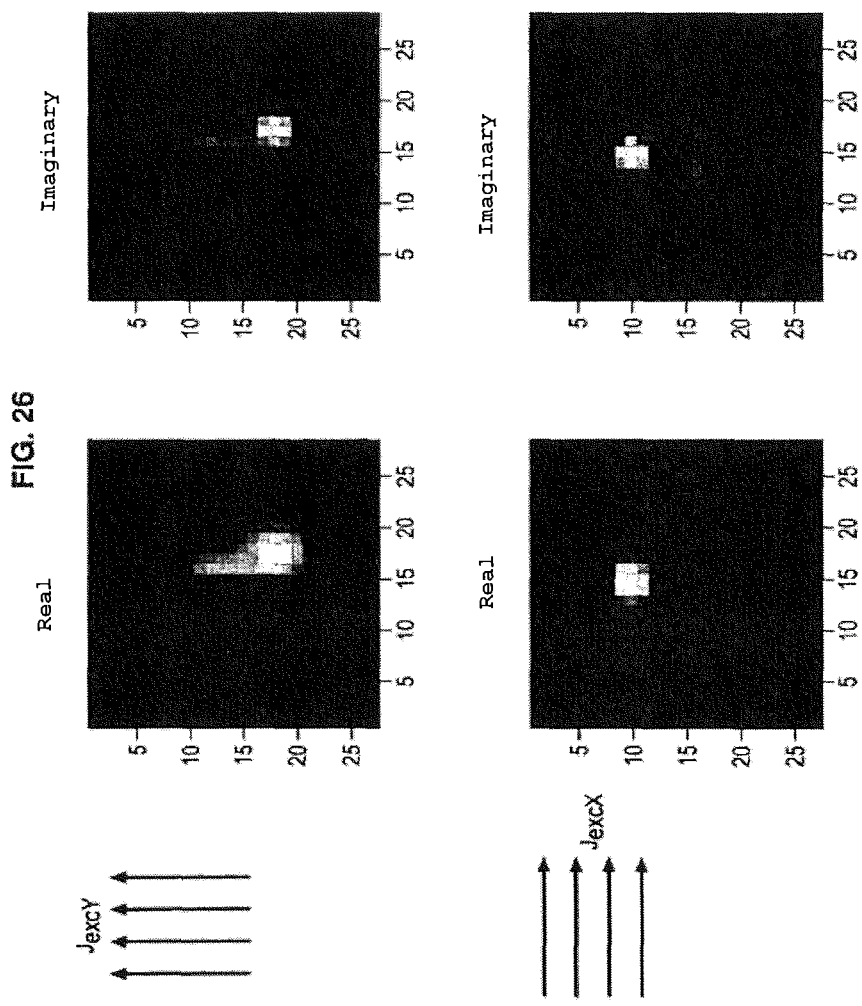
FIGS. 26 to 29 illustrate the results obtained on the plate of FIG. 25 by introducing the notion of rotating field in the method according to the invention.

FIG. 26 shows the field mappings Hz measured at the surface of the target using the ECI imager. Said mappings result from interactions between the excitation currents and the defect, when these are oriented along OY (upper illustrations) and OX (lower illustrations).

Figure 27:
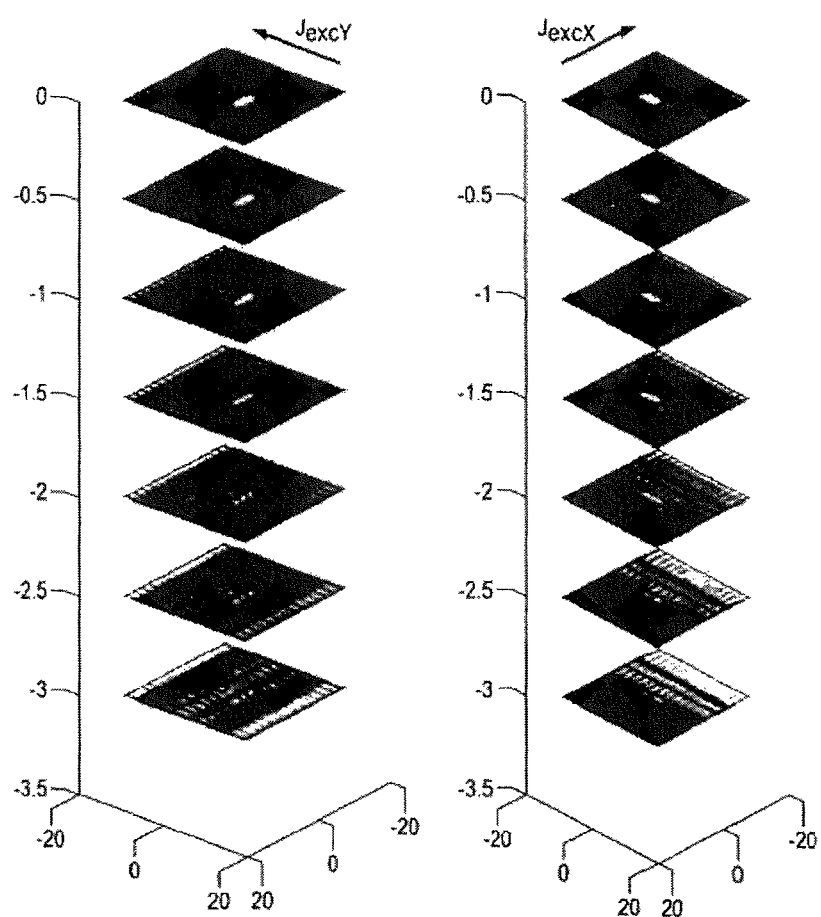

FIG. 27 shows the results of estimating the DPSM current sheets, for different depths, in the case of excitation along OY (left illustrations) and along OX (right illustrations). In both cases, the estimations are obtained without screening. We also remark that the bar of the "T" oriented along OX is particularly well estimated when it is excited along OY, and vice-versa. We also note that the current sheets estimated at depth are not "physical" (no defect greater than 1 mm).

Figure 28:
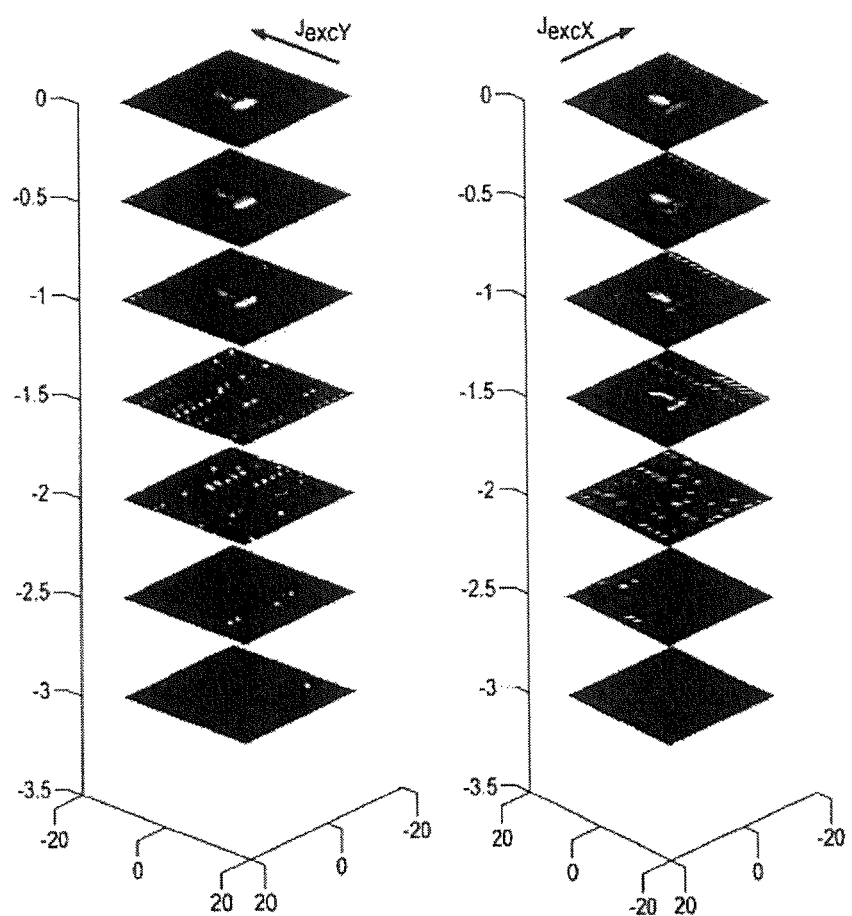

FIG. 28 shows the same estimations, but after screening in module and in phase. The non "physical" current sheets which are estimated at depth are largely eliminated.

Figure 29:
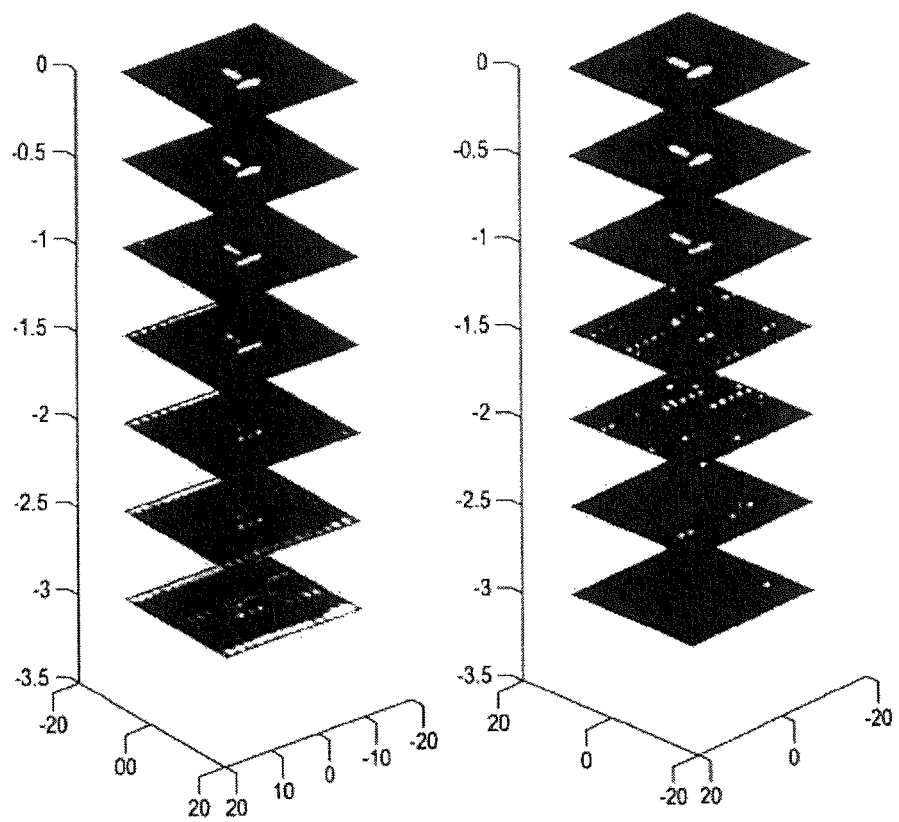

Finally, FIG. 29 shows a result of estimating DPSM current sheets, from results obtained along OX and OY. The "relevant" current sheets obtained in both cases are conserved in the final estimation by means of a principal component analysis (without (on the left) or with (on the right) screening). It may be noted that the estimated current sheets make it possible to visualise the two bars of the "T" with equivalent intensities.

It is clear from these equations that, in a Foucault current device such as the ECI imager that is able to 'illuminate' the object under any angle α in the plane XOY, (in this example, we have assumed in the preceding calculations that the lines of induced currents were oriented along the axis OY, or OX which gives respectively α=π/2 α=0), the variations in σ(x,y) are essentially detectable along the axis transversal to the induced currents (axis OX), and integrated (or filtered, in a more general case) along the other axis (OY).

It should be noted that, more generally, we will consider that the integration along the excitation axis, from −ΔX/2 to +ΔX/2 (respectively ΔY) may comprise a transfer function and become a convolution (for example, in the case of Foucault currents, if we conserve the maximum value of σ(x,y) instead of simply integrating along the axis OX (respectively OY), the impulse response becomes analogous to that of a 'zero order hold'.

If we summarise the preceding concepts by introducing the notion of projection axis or preferential detectability axis, as well as any projection axis $\vec{U}$, we are going to make appear perpendicularly to this axis a projection of σ(x,y) according to a known transfer function (integration or 0 order hold, etc.). On the other hand, we will clearly see the details along the axis transversal to the currents. This comes down to convoluting with a two-dimensional transfer function, having a different resolution along the axes OX and OY. We will consider here that the signal has separability properties.

To give a simple example, if we take the maximal value of σ(x,y) for each value of x, (which corresponds to the shadow borne by σ(x,y) on a plane y=constant), the argument of the integral along the axis OX becomes $\sigma_{maxX}(x,y)$ if the excitation currents are oriented along the axis OX:

$$\sigma_i(x) = \frac{1}{\Delta Y} \cdot \int_{-\Delta Y/2}^{+\Delta Y/2} \sigma_{maxY}(x, y) \cdot dy \quad (27)$$

and $\sigma_{maxY}(x,y)$ along the axis OY if the excitation currents are oriented along OY:

$$\sigma_i(y) = \frac{1}{\Delta X} \cdot \int_{-\Delta X/2}^{+\Delta X/2} \sigma_{maxX}(x, y) \cdot dx \quad (28)$$

For an excitation current oriented along any axis $\vec{U}$ is forming an angle α with the axis OX, we will obtain in the new reference point [U,V] where $\vec{V}$ is perpendicular to $\vec{U}$, of coordinates (u,v):

$$\sigma(v) = \frac{1}{\Delta U} \cdot \int_{-Umin}^{+Umax} \sigma(u \cdot \cos(\alpha) - v\sin(\alpha), u\sin(\alpha) + v\cos(\alpha)) \cdot du \quad (29)$$

I.e.:

$$\sigma(x\sin(\alpha) + y\cos(\alpha)) = \quad (30)$$
$$\frac{1}{\Delta U} \cdot \int_{-Umin}^{+Umax} \sigma(u\cos(\alpha) - v\sin(\alpha), u\sin(\alpha) + v\cos(\alpha)) \cdot du$$

We recover the preceding relations if α=0. For example: U is oriented along the axis OX, V along OY, and this gives:

$$\sigma(y\cos(\alpha)) = \frac{1}{\Delta U} \cdot \int_{-Umin}^{+Umax} \sigma(u\cos(\alpha), v\cos(\alpha)) \cdot du \quad (31)$$

I.e.:

$$\sigma(y) = \frac{1}{\Delta U} \cdot \int_{-Umin}^{+Umax} \sigma(u \cdot v) \cdot du = \frac{1}{\Delta X} \cdot \int_{-\Delta X/2}^{+\Delta X/2} \sigma(x, y) \cdot dx \quad (32)$$

This relation brings us close to conventional tomography methods (X-rays for example), in which an object is 'illuminated' according to different angles: the image results from the integration of the attenuation along the path covered by the excitation beam, but it is well resolved on the transversal axis. The object (σ(x,y) in our case) is then reconstituted by methods such as the inverse Fourier transform for example. Thus, to reconstitute the image of a pixel, we can easily 'enrich' the information by illuminating along a rotating field' Comment: Relations of change of reference point:

$$\begin{pmatrix} x \\ y \end{pmatrix} = \begin{pmatrix} \cos(\alpha) & -\sin(\alpha) \\ \sin(\alpha) & \cos(\alpha) \end{pmatrix} \cdot \begin{pmatrix} u \\ v \end{pmatrix} \quad (33)$$

And:

$$\begin{pmatrix} u \\ v \end{pmatrix} = \begin{pmatrix} \cos(\alpha) & \sin(\alpha) \\ -\sin(\alpha) & \cos(\alpha) \end{pmatrix} \cdot \begin{pmatrix} x \\ y \end{pmatrix} \quad (34)$$

VIII—Fifth Evolution

Tomographic Imaging

This involves proposing, in this evolution of the invention, a generic method for the tomographic analysis of environments, particularly conductors (Foucault current sensors for example). The general principle of such a measurement (whatever the quantity exploited as vector of the electric field, electromagnetic field, ultrasound information, etc.) consists in making this quantity progress along a path on which lies a material, the physical properties of which can vary. The properties in question are linked to the physical quantity used: permittivity for the electric field, conductivity for the Foucault currents, etc. The nature of the 'carrier' wave is chosen as a function of the parameter sought. This generic method consists, from a series of observations made thanks to the sensors, in reconstructing an estimate of the quantity, in cartographic form for example.

Simple Example

Let us begin by considering a simple example (FIG. 30): using a sensor that carries out a measurement for several positions (several paths in our case), we seek to get back to the physical properties of the object (values 'a', 'b', 'c' and 'd', within the 4 pixels represented). In our example, we will consider quite a simple sensor which performs the sum of the values of the properties along the path traversed by the wave. The measured value is inscribed in the bottom or right of the figure. We can carry out a 'vertical' measurement (for a certain position of the measuring device), then carry out a rotation ($\theta=\pi/2$) of the sensor with respect to the object and thereby obtain a 'horizontal' measurement. The results of these measurements (observation vector) may be written in matrix form:

$$\begin{pmatrix} 6 \\ 10 \\ 4 \\ 12 \end{pmatrix} = \begin{pmatrix} 1 & 0 & 1 & 0 \\ 0 & 1 & 0 & 1 \\ 1 & 1 & 0 & 0 \\ 0 & 0 & 1 & 1 \end{pmatrix} \cdot \begin{pmatrix} a \\ b \\ c \\ d \end{pmatrix} \Leftrightarrow OBS = M \cdot A \tag{35}$$

We call M, the transfer matrix of the sensor, observation matrix. This matrix M, although square, is not however inversible: it lacks information because the lines may be linked together, the sums not being weighted differently from one line to the next: in this case, it is necessary to complete all of the measurements, which will give more equations than unknowns.

Figure 30:
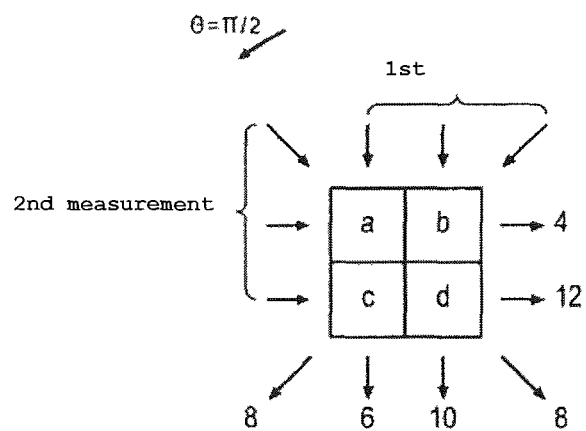
FIG. 30 illustrates a simplified example of tomography using the method according to the invention.

To complete our observable, we add measurements (in diagonal in FIG. 30). Thus, a measurement is now composed of three 'paths', and a rotation of the device allows us to obtain another series of measurements, as in the preceding case.

We will consider in this simple example that the measurements carried out depend directly (and linearly) on the course of the physical quantity employed (electromagnetic or acoustic wave for example): since the diagonal measurements 'travel along' a longer path, we assign $_1\sqrt{2}$ them a coefficient instead of 1 (for illustration purposes).

The transfer matrix M then becomes:

$$M = \begin{pmatrix} \begin{pmatrix} 0 & \sqrt{2} & \sqrt{2} & 0 \\ 0 & 1 & 0 & 1 \\ 1 & 0 & 1 & 0 \end{pmatrix} \\ \begin{pmatrix} \sqrt{2} & 0 & 0 & \sqrt{2} \\ 1 & 1 & 0 & 0 \\ 0 & 0 & 1 & 1 \end{pmatrix} \end{pmatrix} \tag{36}$$

We can still write:

$$OBS = M \cdot A \tag{37}$$

We obtain the values of A by pseudo inverse of M:

$$A = (M^{-1}M)^{-1} \cdot M^{-1} \cdot OBS \tag{38}$$

We indeed find: a=1, b=3, c=5, d=7.

After this example, we give a more 'real' application of this concept, in which we are going to illustrate the adaptation to diffraction tomography, and the exploitation of the DPSM method to identify the observation matrix M in an original manner. Two variants will be presented hereafter, depending on whether there is an access to several faces of a device (as has been presented in the simple example), or instead an access to only one of the faces of a device. This latter point makes it possible to illustrate the application of this tomography method to the Foucault current device described previously, in which the measurement is carried out in a plane xOy at the surface of a metal containing defects or inclusions, and for which we seek an image.

Example

Two or More Accessible Faces

Figure 31:
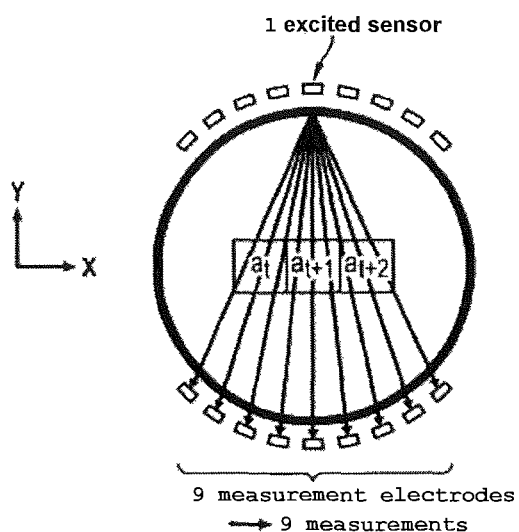
FIG. 31 illustrates an example of electrostatic application of the tomography of FIG. 30.

We will take an interest here in an application in electrostatics with a cylindrical geometry in which we have access, for the measurement, on the perimeter of the geometry (cf. FIG. 31).

We have at our disposal P=9 measurement sensors, of N data to be determined (lesan). For a given position of the electrodes, we write the observation equation which may be formulated in integral form:

$$S(p) = \int_x \int_y h(p, x, y) \cdot a(x, y) \cdot dx dy \tag{39}$$

with $a(x,y)=a_n$ (with each couple (x,y) of the breakdown into pixels is associated an index 15 n).

Comment: the function h(p,x,y) is a transfer function that depends on the measurement position $p(x_p, y_p)$. This function is different for each position p, and is thus not stationary. The function (39) is thus not a convolution. Thus, any attempt of de-convolution by identification of the transfer function would probably be awkward or even impossible.

The discretisation of the domain enables a writing analogous to that employed for the equation (35), by performing a spatial discretisation along $\Delta x$ and $\Delta y$:

$$S(p) = \sum_{n=1}^{N} h(p, n) \cdot a(n) \Delta x \cdot \Delta y \tag{40}$$

For example, in the case of a capacitive sensor, it is possible to write the observation equation in the form:

$$S(p) = \frac{1}{C(p)} = \oint_l \frac{1}{\varepsilon(l)} \frac{1}{s(l)} dl \tag{41}$$

This equation takes account of the variations in permittivity $\varepsilon(l)$ along the path followed by the physical quantity exploited (here an electric field), and since the field lines do not remain strictly parallel, the surface that they occupy s(l) also varies. This writing thus reveals the quantity measured as the placing in series of elementary capacities. It is for this reason that we here use the value $$\frac{1}{C(p)}$$

as information sensor.

This equation may be written by discretising the 'path' $l$:

$$\frac{1}{C(p)} = \sum \frac{1}{\varepsilon(p)} \frac{1}{s(l)} \Delta l \quad (42)$$

After this example, let us return to the general case and express the equation (40) in matrix form:

$$S = M \cdot \begin{pmatrix} a_1 \\ a_2 \\ \vdots \\ a_N \end{pmatrix} = M \cdot A \quad (43)$$

is not a circulant matrix or a Toeplitz matrix.

The observation equation gives information cues. Here, we have at our disposal nine information cues, which is not sufficient for the N unknowns. It is then necessary to enrich the signal (increase of the entropy of the information) by carrying out a new measurement after having turned the sensor by an angle θ (choice, for example, of m measurement positions).

The observation equation (40) would become, if the object had been turned and the fixed sensor left (which comes down to the same thing):

$$S_\theta(p) = \int_x \int_y h(p, x, y) \cdot a(x\cos(\theta) - y\sin(\theta), x\sin(\theta) + y\cos(\theta)) \cdot dx\, dy \quad (44)$$

A change of variable reveals sine and cosine terms in the integral, which then takes the appearance of a Fourier transform.

In our case, we conserve the matrix form of the observation equation, which for each new measurement at angle $\theta_i$ is enriched by a new sub-matrix observation $M_{\theta i}$.

The overall equation, in its matrix form, may thus be written as follows:

$$S = \begin{pmatrix} S_{\theta_1} \\ S_{\theta_2} \\ \vdots \\ S_{\theta_m} \end{pmatrix} = \begin{pmatrix} M_{\theta_1} \\ M_{\theta_2} \\ \vdots \\ M_{\theta_m} \end{pmatrix} \cdot \begin{pmatrix} a_1 \\ a_2 \\ \vdots \\ a_N \end{pmatrix} = Mglobale \cdot \begin{pmatrix} a_1 \\ a_2 \\ \vdots \\ a_N \end{pmatrix} \quad (45)$$

Example

A Single Accessible Face

Let us consider a Foucault current sensor (ECI) briefly returned to in FIG. 32. This figure shows the excitation currents created by inductive coils (not represented here), the material under test and its discretisation with a view to the reconstitution of the image, and the measuring zone (circular in the drawing, and which can represent the garnet of the MOI). Here, the observation vector is constituted of the quantity that one can observe at the surface with the magneto-optic garnet: the field $H_z$. We have at our disposal P measurement points spread out on the sensitive surface. Our vector of unknowns is the quantity σ(x,y) linked to a discretisation (Δx, Δy) placed in lexical form σ(n). In order to enrich the information, as previously, we change the angle of incidence of the excitation currents.

By doing this, we can obtain a matrix relation between our observation and our unknowns: this equation is identical to equation (45).

The matrix M is thus defined by the relation (45), for an orientation of the excitation currents $\theta_i$:

$$S = M_{\theta_i} \cdot A \Leftrightarrow S = \begin{pmatrix} M_{11} & M_{12} & M_{13} & \ldots & M_{1N} \\ M_{21} & M_{22} & M_{23} & \ldots & M_{2N} \\ M_{31} & M_{32} & M_{33} & \ldots & M_{3N} \\ \vdots & \vdots & \vdots & & \vdots \\ M_{P1} & M_{P2} & M_{P3} & \ldots & M_{PN} \end{pmatrix} \cdot \begin{pmatrix} a_1 \\ a_2 \\ a_3 \\ \vdots \\ a_N \end{pmatrix}$$

When all of the values of the pixels $a_i$, are identical and correspond to the conductivity value $\sigma_0$, the excitation currents are not deviated and no field component normal to the surface appears. It is thus more logical to define a(n) from variations in σ(n) with respect to $\sigma_0$ (simply by convention):

$$a(n) = \frac{\sigma_0 - \sigma(n)}{\sigma_0} \quad (47)$$

Using the DPSM model, we are going to carry out a series of N modelling operations, in which we are going to displace a small defect at σ(n)=0, thus a(n)=1, in an environment at σ(k≠n)=$\sigma_0$ The relation (46) becomes, if, for example, the pixel No 3 is the small defect:

$$S = M_{\theta_i} \cdot A \Leftrightarrow S = \begin{pmatrix} M_{11} & M_{12} & M_{13} & \ldots & M_{1N} \\ M_{21} & M_{22} & M_{23} & \ldots & M_{2N} \\ M_{31} & M_{32} & M_{33} & \ldots & M_{3N} \\ \vdots & \vdots & \vdots & & \vdots \\ M_{P1} & M_{P2} & M_{P3} & \ldots & M_{PN} \end{pmatrix} \cdot \begin{pmatrix} a_1 = 0 \\ a_2 = 0 \\ a_3 = 1 \\ \vdots \\ a_N = 0 \end{pmatrix} \quad (48)$$

In this case, the output vector, S, is equal to the third column of M:

$$S = M_{\theta_i} \cdot A \Leftrightarrow S = \begin{pmatrix} M_{13} \\ M_{23} \\ M_{33} \\ \vdots \\ M_{P3} \end{pmatrix} \quad (49)$$

Thus, the entire matrix M may be identified, column by column, from the DPSM model which is easy to parameterise, and makes it possible to create experience plans.

In the case where there is an access to two faces of a problem to carry out measurements, we discretise along x and y, and we can obtain a third dimension by progressing by step Δz along the generator, (along the axis z). This makes it possible to obtain three-dimensional images, discretised along the voxels Δx, Δy and Δz.

In Foucault current imaging, as the system is described here (and corresponds to the majority of cases), we only have access to a single face, discretised along Δx and Δy. The access to a quantity Δz may be achieved as presented in the preceding point VI, by carrying out several measurements at several frequencies (cf. the multi-frequency equation, recalled here for memory):

$$\begin{bmatrix} \vec{H}_{F1} \\ \vec{H}_{F2} \\ \vec{H}_{F3} \end{bmatrix} = \Delta V \cdot \qquad (22)$$

$$\begin{bmatrix} M_{11} \cdot \mathrm{diag}(Q_{11} \cdot I_1) & M_{12} \cdot \mathrm{diag}(Q_{21} \cdot I_1) & M_{13} \cdot \mathrm{diag}(Q_{31} \cdot I_1) \\ M_{21} \cdot \mathrm{diag}(Q_{12} \cdot I_2) & M_{22} \cdot \mathrm{diag}(Q_{22} \cdot I_2) & M_{23} \cdot \mathrm{diag}(Q_{32} \cdot I_2) \\ M_{31} \cdot \mathrm{diag}(Q_{13} \cdot I_3) & M_{32} \cdot \mathrm{diag}(Q_{23} \cdot I_3) & M_{33} \cdot \mathrm{diag}(Q_{33} \cdot I_3) \end{bmatrix} *$$

$$\begin{bmatrix} \vec{\sigma}_1 \\ \vec{\sigma}_2 \\ \vec{\sigma}_3 \end{bmatrix}$$

It should be recalled that the quantities $\vec{\sigma}_1$, $\vec{\sigma}_2$, $\vec{\sigma}_3$ represent the values of the differences in conductivities within voxels resulting from the breakdown into $\Delta x$ and $\Delta y$ of layers XoY situated at depths k=1, 2, and 3 (spaced vertically by $\Delta z$). The matrices $M_{ik}$ are the direct DPSM matrices, which connect small variations of currents in said voxels to the field $\vec{H}_{F1}$ measured at the surface, for an excitation at the frequency $F_i = F_1$, then $F_2$, $F_3$, etc.

The matrices $Q_{ik} \cdot I_k$ represent the excitation conditions (excitation current in each voxel of the layer No k for a frequency F index i).

The idea developed here takes up exactly this concept, and makes it possible to extend it to the case where the object is illuminated under different incidence angles: the blocks of matrices $M_{ki} \cdot \mathrm{diag}(Q_{ik} \cdot I_k)$ (which connect in the preceding equation the measurement $\vec{H}_{F1}$ carried out at the index frequency i to the properties of the voxels situated in the layer No k) are then constituted for each couple i,k by the Mglobal matrix of equation (45), calculated for a frequency $F_i$, and for a small variation displaced in a layer at depth k. This method, at variable incidence angle, enriches the entropy of the equation (22) as it enriches that of the equation (43).

Furthermore, it is possible to carry out an estimation of the block matrices other than by making an approximation on small variations in current locally induced by the variations in conductivity, as described in the first part of this description. In fact, by assuming the system linear, it is possible to displace a voxel characterised by a conductivity different to that of the material to evaluate all of the terms of the global matrix. This approach calls on the DPSM model for example (a voxel of cubic shape is drawn and it is made to successively cover all of the volumetric meshes drawn in the material), and may also be carried out experimentally.

The advantage of the method described here is that it is also possible to develop a particular breakdown (thus not necessarily performed on the basis of cubic voxels), adapted to the specific geometry of a problem: if we have to image an object stratified in parallel planes (composite carbon material or assembly of riveted sheets for example), the vector of unknowns will be uniquely constituted of the values of the properties of the material in said strata. For an object with symmetry of revolution or comprising a reaming, we could imagine a breakdown into cylindrical coordinates, etc.

It should also be noted that, to limit the effect of potential non-linearities, it is possible to position oneself around a standard configuration to identify the terms of the preceding Mglobal matrix. In this standard configuration, to each voxel (index n) is assigned a physical property $a_n$, which leads, through simulation or experimentation, to an observation vector $S_{standard}$. We then identify each column (index n) of the matrix by means of a small additive variation $\Delta a_n$ of the properties of the voxel of index n:

$$S_{standard} = M_{\theta_i} \cdot A_{standard} \Leftrightarrow S \qquad (50)$$

$$= \begin{pmatrix} M_{11} & M_{12} & M_{13} & \ldots & M_{1N} \\ M_{21} & M_{22} & M_{23} & \ldots & M_{2N} \\ M_{31} & M_{32} & M_{33} & \ldots & M_{3N} \\ \vdots & \vdots & \vdots & & \vdots \\ M_{P1} & M_{P2} & M_{P3} & \ldots & M_{PN} \end{pmatrix} \cdot \begin{pmatrix} a_1 \\ a_2 \\ a_3 \\ \vdots \\ a_N \end{pmatrix}$$

$$S = M_{\theta_i} \cdot A \Leftrightarrow S \qquad (51)$$

$$= \begin{pmatrix} M_{11} & M_{12} & M_{13} & \ldots & M_{1N} \\ M_{21} & M_{22} & M_{23} & \ldots & M_{2N} \\ M_{31} & M_{32} & M_{33} & \ldots & M_{3N} \\ \vdots & \vdots & \vdots & & \vdots \\ M_{P1} & M_{P2} & M_{P3} & \ldots & M_{PN} \end{pmatrix} \cdot \begin{pmatrix} a_1 \\ a_2 \\ a_3 + \Delta a_3 \\ \vdots \\ a_N \end{pmatrix}$$

$$S - S_{standard} = M_{\theta_i} \cdot (A - A_{standard}) = \Delta a_3 \cdot \begin{pmatrix} M_{13} \\ M_{23} \\ M_{33} \\ \vdots \\ M_{P3} \end{pmatrix} \qquad (52)$$

For example, if we are looking for corrosion or small cracks on a riveted assembly, we outline the normal configuration, which gives the vector $S_{standard}$, then we calculate M for small variations in conductivity of each of the voxels. The Mglobal matrix is then composed from all the matrices $M_{\theta_i}$, corresponding to a measurement under incidence angle $\theta_i$.

Figure 34A:
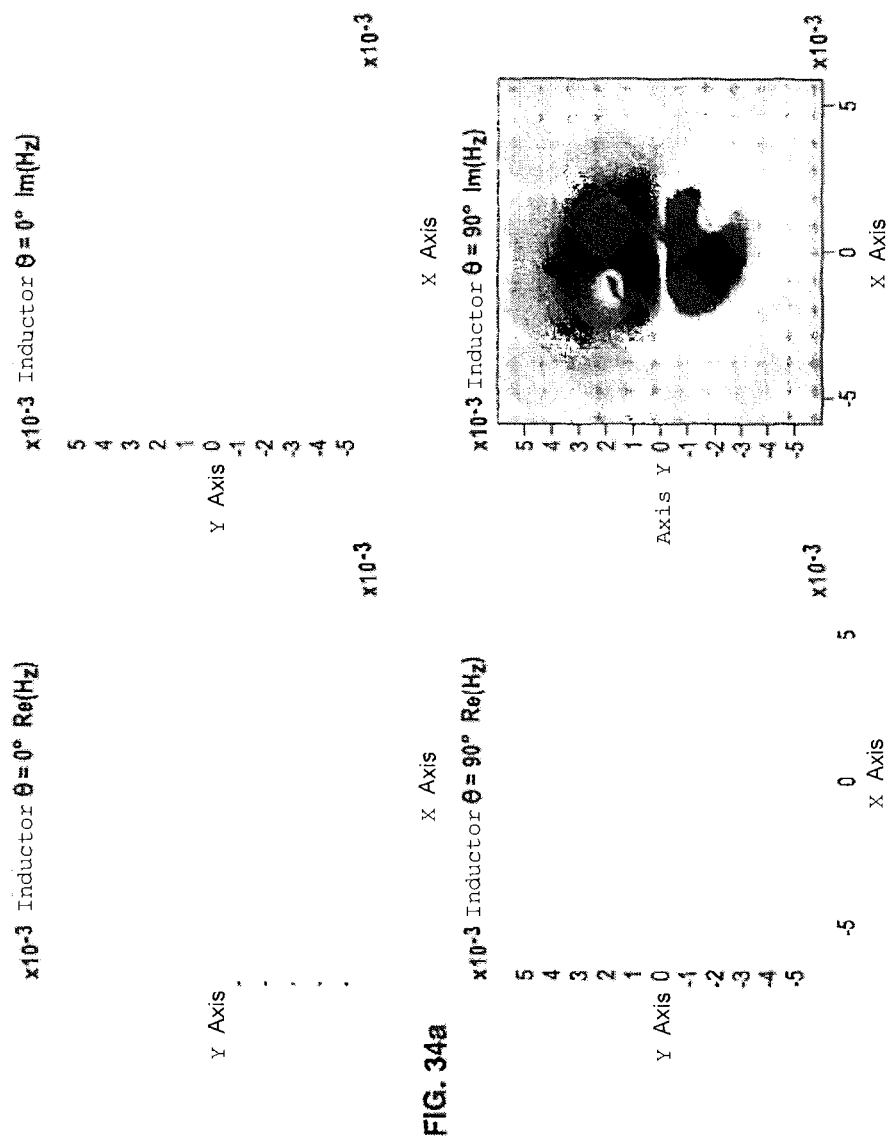
Figure 34B:
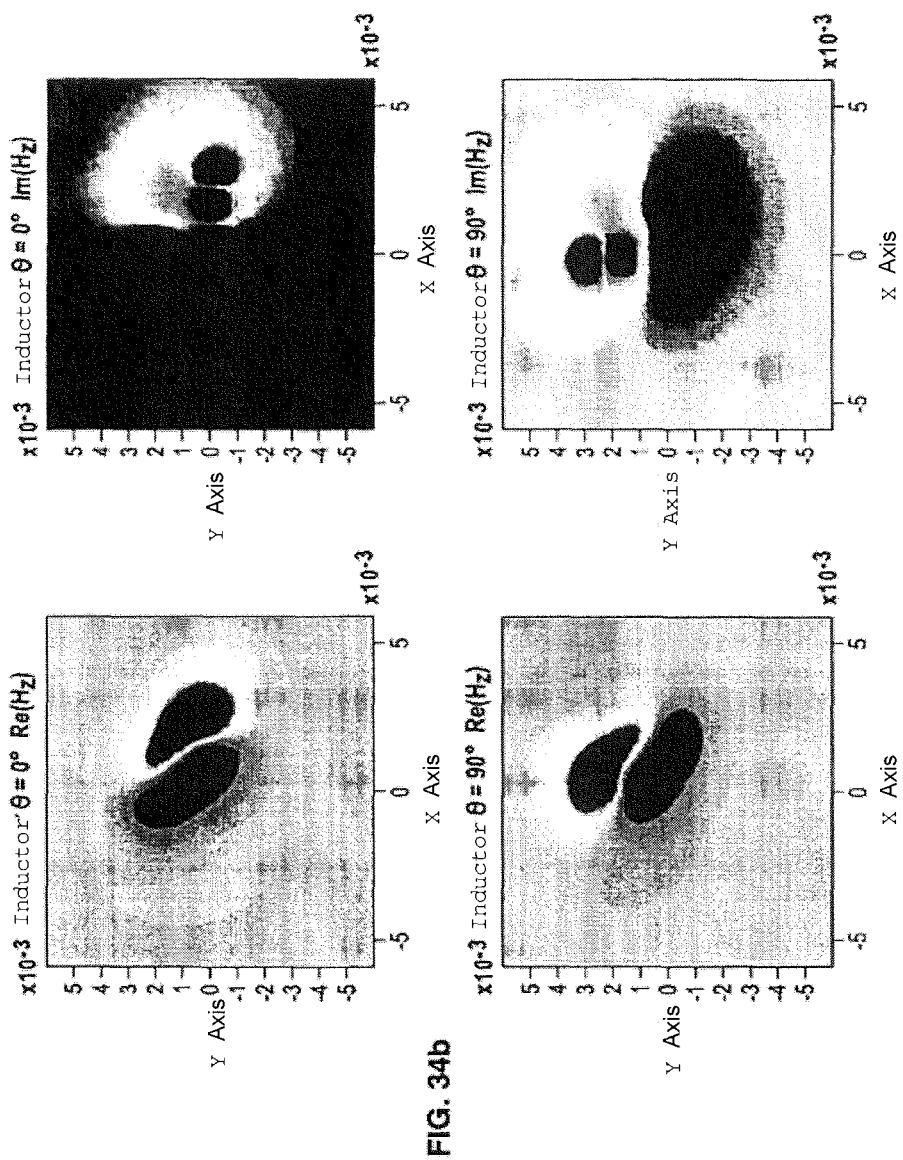

Examples with Capsule Shaped Defects i. In FIGS. 33 to 35, we illustrate the application of the method to a capsule shaped defect at 45° in a block of aluminium, thus conductive material. The advantage of the capsule shape is it represents quite well defects of crack type that it is possible to encounter in NDC. In a first series a, the capsule is centred, whereas in the second series b, the capsule is not centred. FIG. 33 illustrates the test geometry. FIG. 34 represents images obtained in the two series a and b with an inductor at 0° and at 90°. FIG. 35 shows the result of the inversion test in the two series a and b by the method according to the invention. It may be clearly seen that the capsule shaped defect is well identified and spatially pinpointed in the block of material tested.

During these tests, the robustness and the reliability of the method was demonstrated by making noisy the images of FIG. 34. The method always gives good reliable results with a signal to noise ratio greater or equal to around 0.1.

IX—Production of a Device Able to Implement the Method According to the Invention The production of a device intended to implement the method according to the invention that has been described will now be briefly outlined. Such a device comprises an instrumental system and a module of automatic estimation of defects, in this case serving as example of the Foucault current imaging technique.

The device, here in this example, comprises an ECI imager (described in the documents WO2005/001467 and WO 2007/135265, to which it is possible to refer for further information), with which is associated a computer (of PC type for example) hosting a human machine interface (HMI) making it possible to configure and manage the acquisition of magnetic field images and to perform the automatic estimation and the visualisation of defects.

The module for automatically estimating defects may operate, preferably, in real time, in other words the defect estimation takes place as the FC (Foucault current) images are acquired. In fact, knowing the structure to be inspected (for example aeronautic riveted joint, the defect-free constitution of which is known), it is possible to pre-calculate the matrices of couplings required for the implementation of the method according to the invention, at the excitation frequencies considered relevant. Consequently, it is possible to carry out the estimation of the sources from the DPSM method in real time from these pre-established matrices.

Generally speaking, the method according to the invention that we have described thus enables the quantitative estimation of defects by NDE by recovering the characteristics of a defect from observations of a physical quantity made at the surface of the structure, and knowledge of the interactions between the object to be characterised (the defect) and the wave emitted by the device implementing said method according to the invention.

At present, in practice, this estimation is only possible in trivial cases, firstly because the problem is "poorly posed" (the available observations are insufficient to "get back to" the properties of the object sought) and then because we do not have, in the general case, an analytical expression of the interactions that is inversible.

It is then possible to perform a numerical or semi-analytical modelling of the interactions, and the implantation of an iterative algorithm for adjusting the parameters of the model so that the system approaches as best as possible the observations. After convergence of said optimisation algorithm, the estimated parameters make it possible to characterise the defect. This approach nevertheless requires an implementation that is very costly in calculation time (exhaustive and therefore cumbersome models of interactions, iterative method) and poses the problem of the convergence and the robustness of the iterative algorithm, the resolution of which requires the introduction of knowledge a priori more or less considerable on the defect sought. Nevertheless, it is rarely implemented from experimental data, and is not very compatible with an industrial exploitation, in particular in the field of NDE by Foucault currents.

Other methods, more pragmatic, and heavily employed, consist in working from defect data bases either to restrict the investigation space of the inversion, or instead to carry out a "partial" inversion of the signals provided by the instrumental system; it then involves identifying defects of known types by comparison of their "signature" (typical Foucault currents signal provided by the instrumental system for a given defect) with those present in the data base. It generally involves proceeding in the following manner:

extracting one or more "relevant" parameters of the defect signature,
from which is carried out an estimation of one or more defect characteristics (presence, depth, length, etc.) is carried out.

A large variety of parameters and identification techniques may be employed. A variant consists in constructing a behavioural model (black box) of the instrumental system/defect interactions, again through learning from a data base. The estimation of one or more parameters of the defect considered takes place by interpolation or generalisation of the known configurations of defects, for example using artificial neuronal networks. Nevertheless, inversion results remain partial, in so far as it only goes up to a reduced number of characteristics of defects. These methods, efficient when they involve detecting a given defect, or instead discerning classes of pre-defined defects, prove nevertheless not to be very robust when unexpected situations are encountered (defect too dissimilar to those contained in the data base, noisy experimental data), and do not enable a quantitative estimation of the defects. Moreover, they require the creation of extended data bases (potentially difficult to develop for complex geometries) and the implementation of learning techniques, as well as calibration phases for an experimental utilisation. These methods are therefore not general solutions to the problem of the defect estimation by Foucault currents.

A combination of these two approaches has been proposed in the document FR2885697. It consists in carrying out a linear estimation of the instrumental system/defect interactions, in the case of a known defect (estimated interactions model, calibration), then carrying out an estimation of unknown defects by resolving the inverse linearized problem. To date, this approach has only proved to be convincing for the estimation of emerging defects of groove type, the properties of which are close to those of the defects used for the calibration. Furthermore, the inversion process has the same drawbacks as those described previously, linked to the problems of duration, convergence and robustness of the iterative method used.

The method according to the invention enables the above mentioned problems to be resolved. As we have seen, the method according to the invention is based on the DPSM method (described in greater detail in the documents WO2004/044790 and WO2007/071735, to which it is possible to refer for further information) for which the coupling matrices that model the interactions in the environments can be pre-calculated for the configuration of the inspected structure. It ensues that the method for estimating defects according to the invention can be carried out in real time, as the images supplied by the instrumental system are acquired.

Moreover, the method according to the invention does not require the constitution of defect data bases, or knowledge a priori of the shape and the position of the defect encountered: simple to implement, it resolves the problem of robustness vis-à-vis atypical situations.

The method according to the invention does not amount to the estimation of one or more characteristics of the defect. It makes a three-dimensional "reconstruction" of the defect, whatever the shape. It therefore has a considerable capacity for generalisation.

Moreover, the first tests carried out from experimental data in Foucault currents (which served as examples for describing the method according to the invention) have proved the robustness of the technique vis-à-vis the measurement noise.

The method according to the invention is thus perfectly compatible with an industrial exploitation.

Finally, it should be noted that the method according to the invention may be easily enriched by a multi-frequency, impulsive, multi-orientation, and even multi-technique approach (Foucault currents/ultrasounds, electric/electromagnetic, etc.), thanks to the generic character of its formulation. Nevertheless, since the method according to the invention is generic and multi physical, other NDE applications are also targeted, such as ultrasound, electrostatic, acoustic, thermal, photo-thermal imaging techniques, etc., as well as coupled techniques (multi-physical). The field of acoustic microscopy is also an immediate area of application of the invention. Moreover, this technique will find applications in closely related fields, such as RADAR or SONAR imaging, or instead geophysics . . . .

We have seen that the method according to the invention differs from techniques currently employed for the estimation of defects in structures in that:

- it can be exploited in real time (during acquisitions of data)
- it does not require an iterative estimation algorithm,
- it does not require the construction of defect data bases
- it does not require knowledge a priori of the shape or the localisation of the defect searched for
- it is robust to the noise of the experimental data
- it may be easily automatable
- it exploits in an original manner a wave/environment interaction model, itself original The method according to the invention thus resolves the problems linked to the lack of robustness, difficulty of implementation, and lack of generalisation of the techniques commonly employed. It also becomes free of prohibitive calculation times and the necessity of knowledge a priori, which makes the most elaborate methods difficult to implement in industrial context.

The advantages of the method according to the invention are linked to the performances thereof (rapidity and capacity of generalisation of the defect estimation) as well as the simplicity of implementation thereof. The method according to the invention could be easily exploitable in an industrial context, and has very noticeable advantages in terms of security (quantitatively estimating defects in structures) and economy. As regards this latter point, a high gain may be expected from the use of the method according to the invention, in so far as a rapid and quantitative estimation of the defects makes it possible to reduce the costs and the number of inspections, and to optimise the maintenance and the life cycle of industrial structures.

Obviously, it is possible to make numerous modifications to the invention without however going beyond the scope thereof.

The invention claimed is:

1. Method for quantitatively estimating defects potentially present in an object comprising at least one outer surface, wherein the method comprises the steps of:
   a) "illuminating" the outer surface of the object with an inductive wave field at a predetermined frequency;
   b) measuring, at the outer surface of the object, an induced wave field ($\vec{H}$);
   c) developing, from the properties of the object's material, a coupling matrix T associated with a depth Z of the object from the outer surface;
   d) solving the matrix system $$\left( \begin{bmatrix} \vec{H} \\ \vec{0} \\ \vec{0} \end{bmatrix} \right) = T \cdot \vec{J}$$

in order to determine a vector $\vec{J}$ at depth Z;

e) extracting a sub-vector $\vec{J}_S$ of the vector $\vec{J}$, corresponding to a potential defect on the object at depth Z; and
   f) quantitatively estimating the potential defect from the sub-vector $\vec{J}_S$ at depth Z, wherein the method is performed using a computer or processor.

2. A method according to claim 1, wherein, during step f), a sub-step f1) of screening is carried out in order to only keep the components of the sub-vector $\vec{J}_S$ of which a phase and a module of the induced wave field at depth Z, which said components represent, are in harmony with those of the inductive wave field.

3. A method according to claim 1, wherein, for a depth Z, the steps a) to f) are carried out for at least two "illuminating" orientations of the outer surface of the object with an inductive wave field.

4. A method according to claim 3, wherein the at least two estimations obtained according to the at least two "illuminations" are merged by means of a principal components analysis to obtain a quantitative estimation of the potential defect at depth Z.

5. A method according to claim 1, further comprising a step of three-dimensional reconstruction of the potential defect by repeating n times the steps a) to f) for n separate depths Z.

6. A method according to claim 5, wherein, during the step of three-dimensional reconstruction, a prior sub-step of progressive screening is carried out to perform the n quantitative estimations.

7. A method according to claim 6, wherein, for an iteration p, 1<p<=n, from the field measurement $\vec{H}(Z_p)$ is subtracted all or part $\vec{H}_z'(Z_{p-1})$ of the screened field measurement $\vec{H}(Z_{p-1})$, according to the formula $\vec{H}(Z_p) = \vec{H}^{relevé}(Z_p) - K \cdot \vec{H}'(Z_{p-1})$, where K is a re-injection coefficient comprised between 0 and 1 and $\vec{H}^{relevé}(Z_p)$ is the measurement of step b).

8. A method according to claim 7, wherein the components of $\vec{H}_z'(Z_{p-1})$ correspond to the potential defect estimated during the iteration p−1, or to the edges of said defect.

9. A method according to claim 1, wherein, for a given depth Z, a specific predetermined frequency is associated for the inductive wave field used in step a).

10. A device for quantitatively estimating defects potentially present in an object comprising means for emitting an inductive wave field, means for recording a measurement of an induced wave field on a surface of the object, and processing means configured to implement a method for quantitatively estimating defects potentially present in an object comprising at least one outer surface, wherein the method comprises the steps of:
   a) "illuminating" the outer surface of the object with an inductive wave field at a predetermined frequency;
   b) measuring, at the outer surface of the object, an induced wave field ($\vec{H}$);
   c) developing, from the properties of the object's material, a coupling matrix T associated with a depth Z of the object from the outer surface;
   d) solving the matrix system $$\left( \begin{bmatrix} \vec{H} \\ \vec{0} \\ \vec{0} \end{bmatrix} \right) = T \cdot \vec{J}$$

in order to determine a vector $\vec{J}$ at depth Z;

e) extracting a sub-vector $\vec{J}_S$ of the vector $\vec{J}$, corresponding to a potential defect on the object at depth Z; and
   quantitatively estimating the potential defect from the sub-vector $\vec{J}_S$ at depth Z.

* * * * *